United States Patent [19]

Cucin

[11] Patent Number: 5,795,323
[45] Date of Patent: Aug. 18, 1998

[54] POWER-ASSISTED LIPOSUCTION INSTRUMENT AND CANNULA ASSEMBLY THEREFOR

[76] Inventor: Robert L. Cucin, 8 E. 62nd St., New York, N.Y. 10021

[21] Appl. No.: 882,927

[22] Filed: Jun. 26, 1997

Related U.S. Application Data

[63] Continuation of Ser. No. 307,000, Sep. 16, 1994, Pat. No. 5,643,198, which is a continuation of Ser. No. 627,240, Dec. 14, 1990, Pat. No. 5,348,535.
[51] Int. Cl.$^6$ ..................................................... A61B 17/20
[52] U.S. Cl. ........................................... 604/22; 604/902
[58] Field of Search ................................. 604/22, 35, 119, 604/268, 902; 606/167, 170, 171, 177; 128/751, 752, 755, 758

[56] References Cited

U.S. PATENT DOCUMENTS 4,909,249   3/1990   Akkas et al. ............................. 606/107

Primary Examiner—Corrine M. McDermott
Attorney, Agent, or Firm—Hopgood, Calimafde, Kalil & Judlowe, LLP

[57] ABSTRACT

A method and apparatus is disclosed for mechanically-assisted liposuction treatment. The apparatus includes a hand-holdable housing, a cannula assembly, and a reciprocation mechanism. The hand-holdable housing has a cavity adaptable for receipt of a portion of the cannula assembly. The cannula assembly includes an inner cannula and an outer cannula, each having a distal end and a proximal end and at least one aspiration aperture about the distal end. The inner cannula is disposed within the outer cannula and the inner and outer aspiration apertures are in at least partial registration to form an effective aspiration aperture. The reciprocation mechanism is disposed within the housing and is operably associated with either the inner or outer cannula so that one of the cannulas can be selectively caused to reciprocate relative to the housing while the other is stationarily disposed relative to the housing. As one of the cannulas is caused to reciprocate relative to the other the effective aspiration aperture formed through the distal end of the cannula assembly, is caused to undergo periodic displacement. In the preferred embodiments, the amount and rate of such aspiration aperture displacement is controllably adjustable. The cannula assembly is releasably detachable from the hand-holdable housing to facilitate cleaning and sterilization of the cannula assembly and the housing.

4 Claims, 9 Drawing Sheets

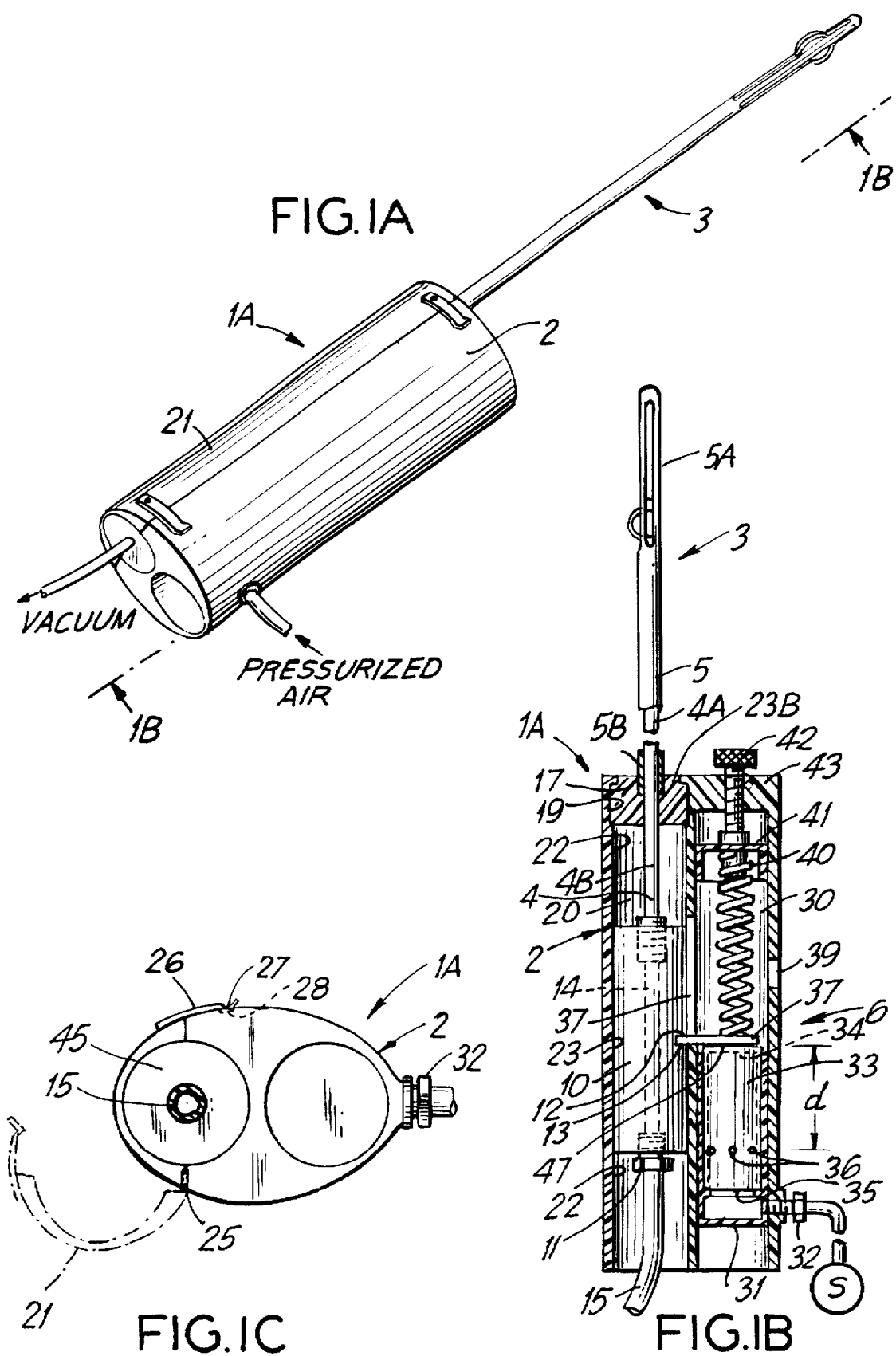

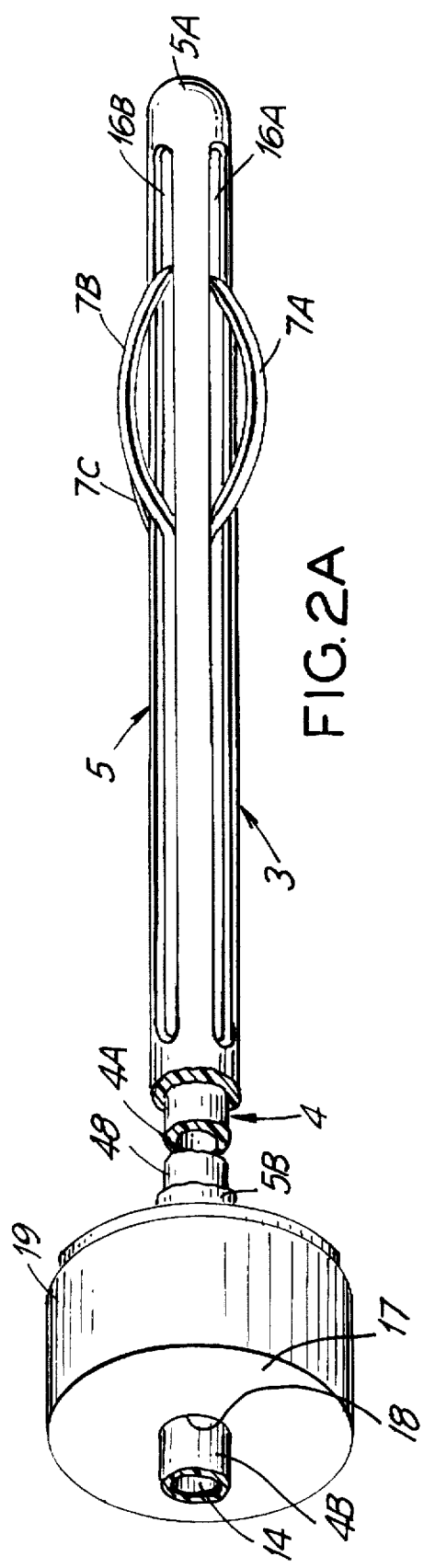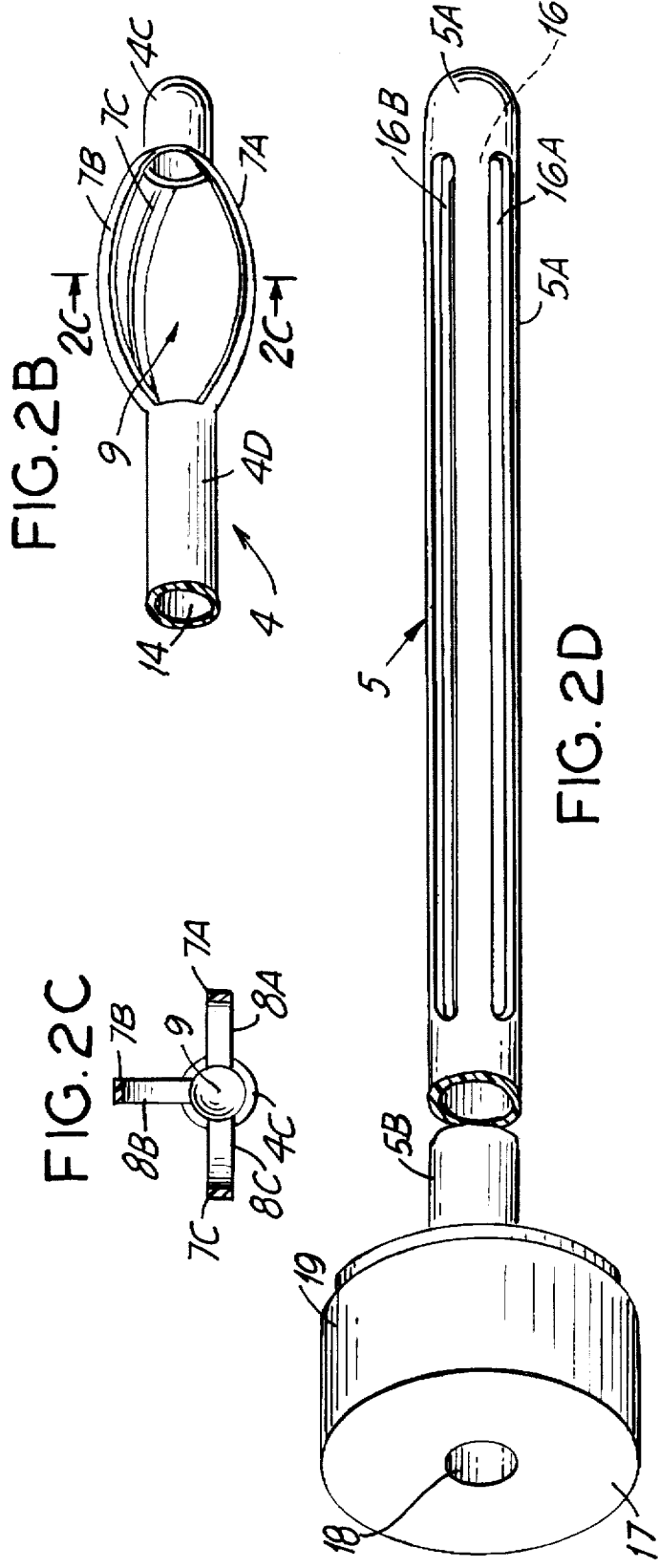

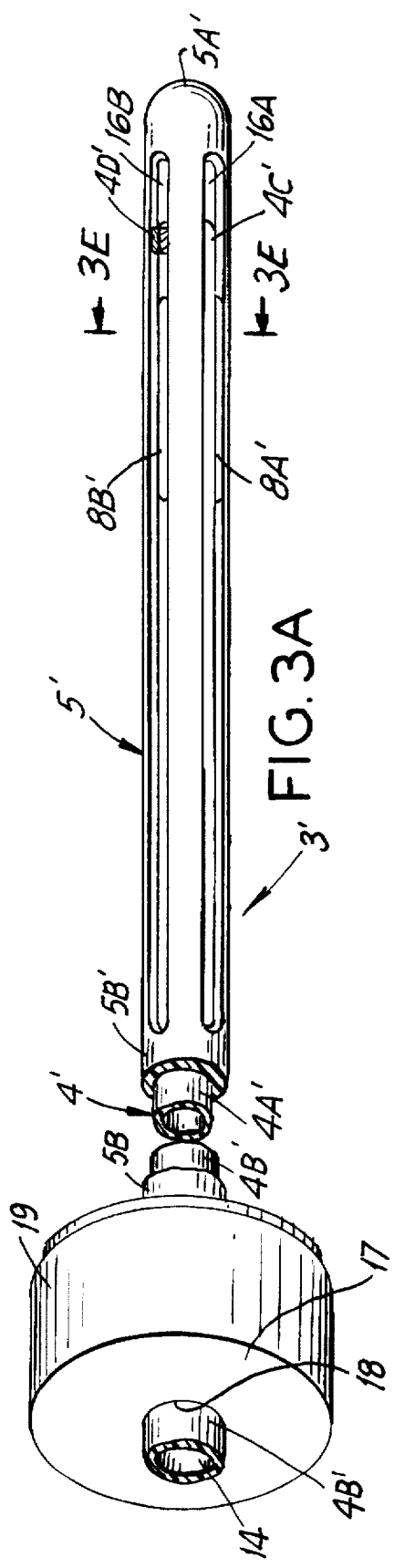
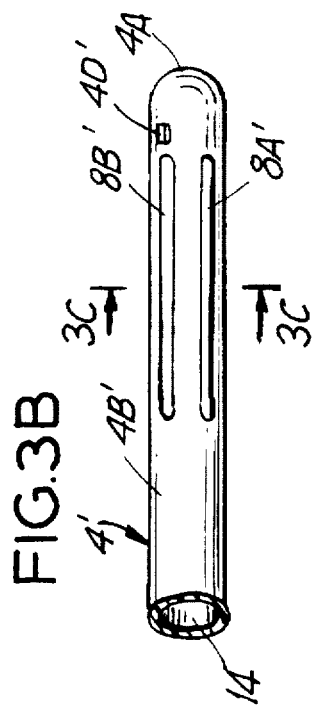
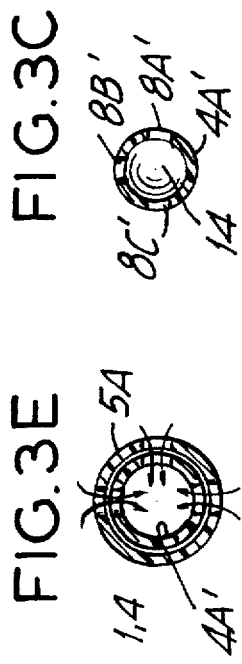
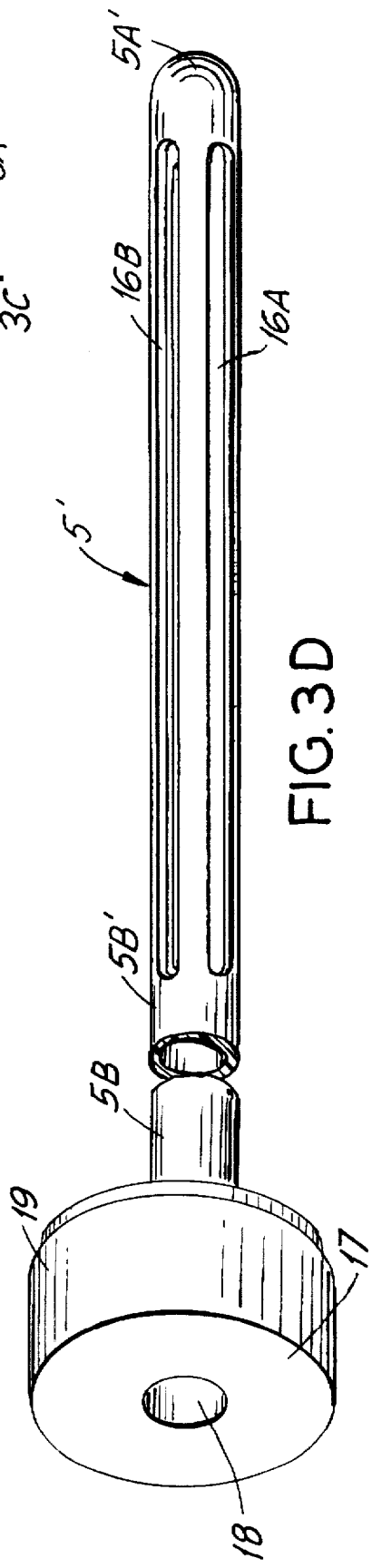
FIG.3A
FIG.3B
FIG.3C
FIG.3D
FIG.3E

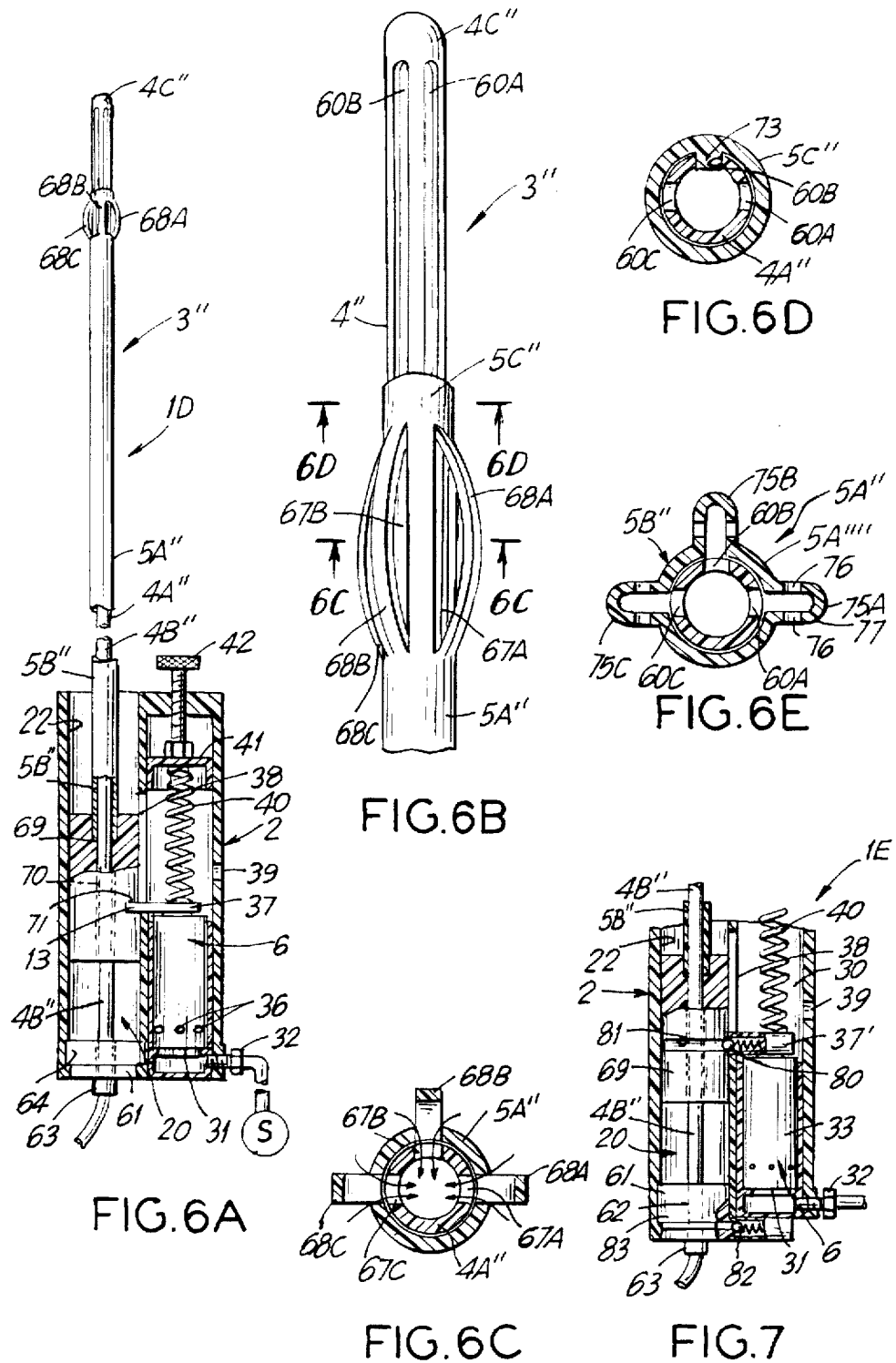

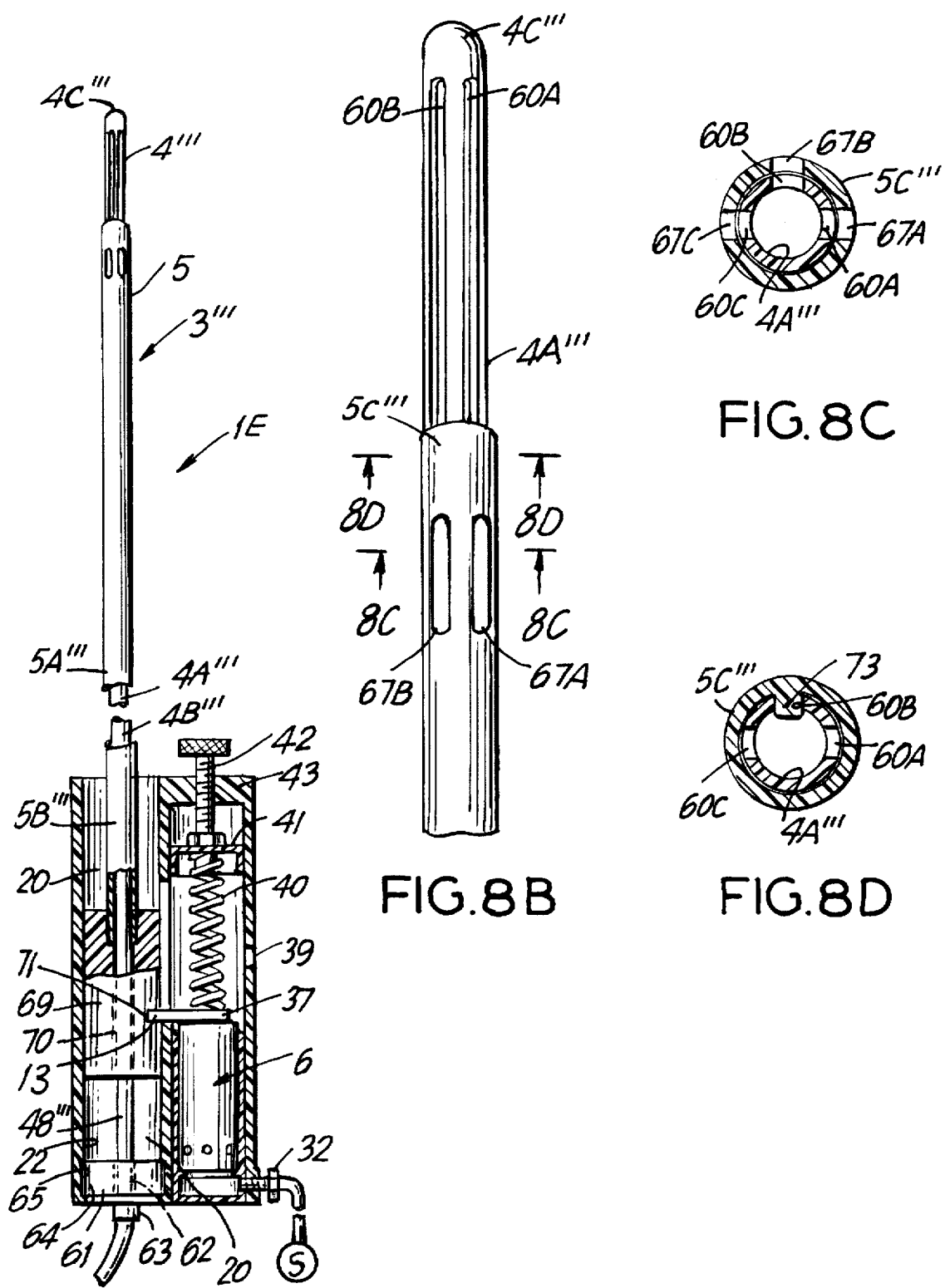

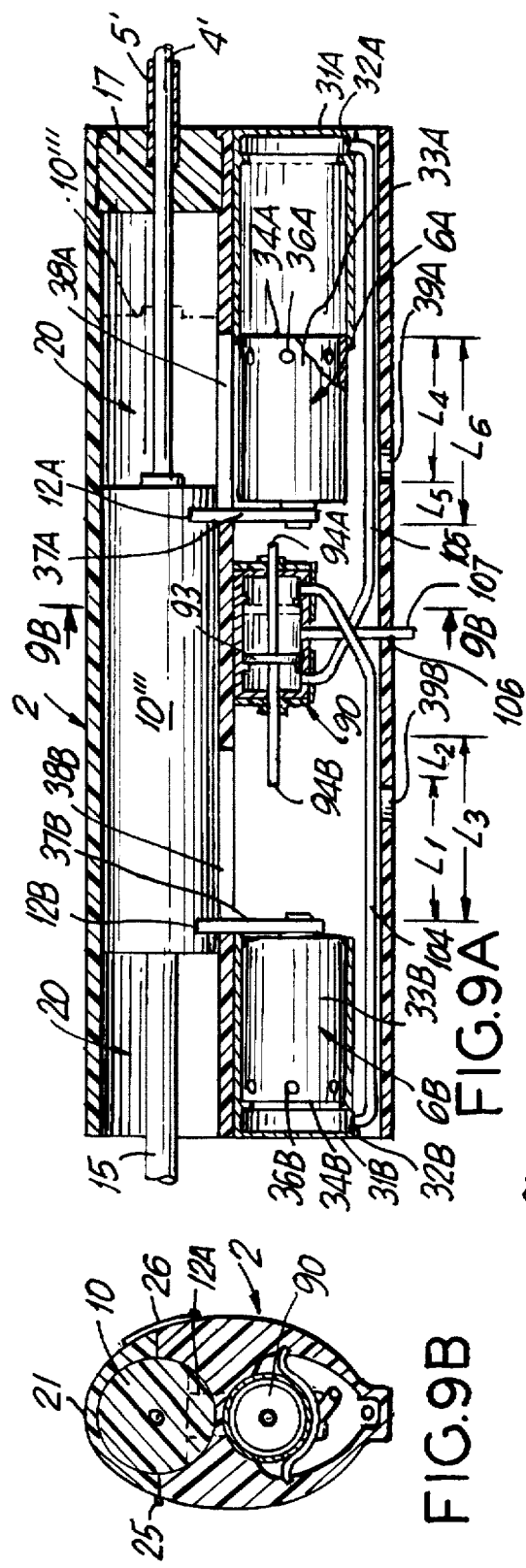
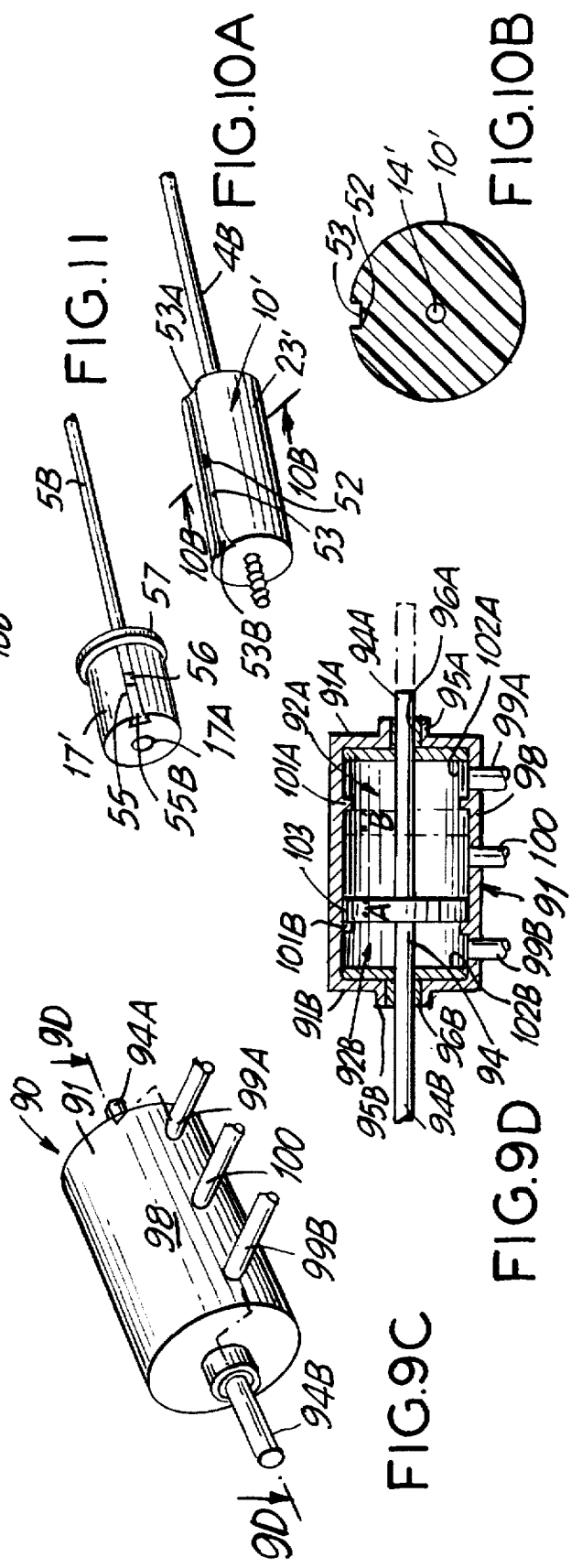

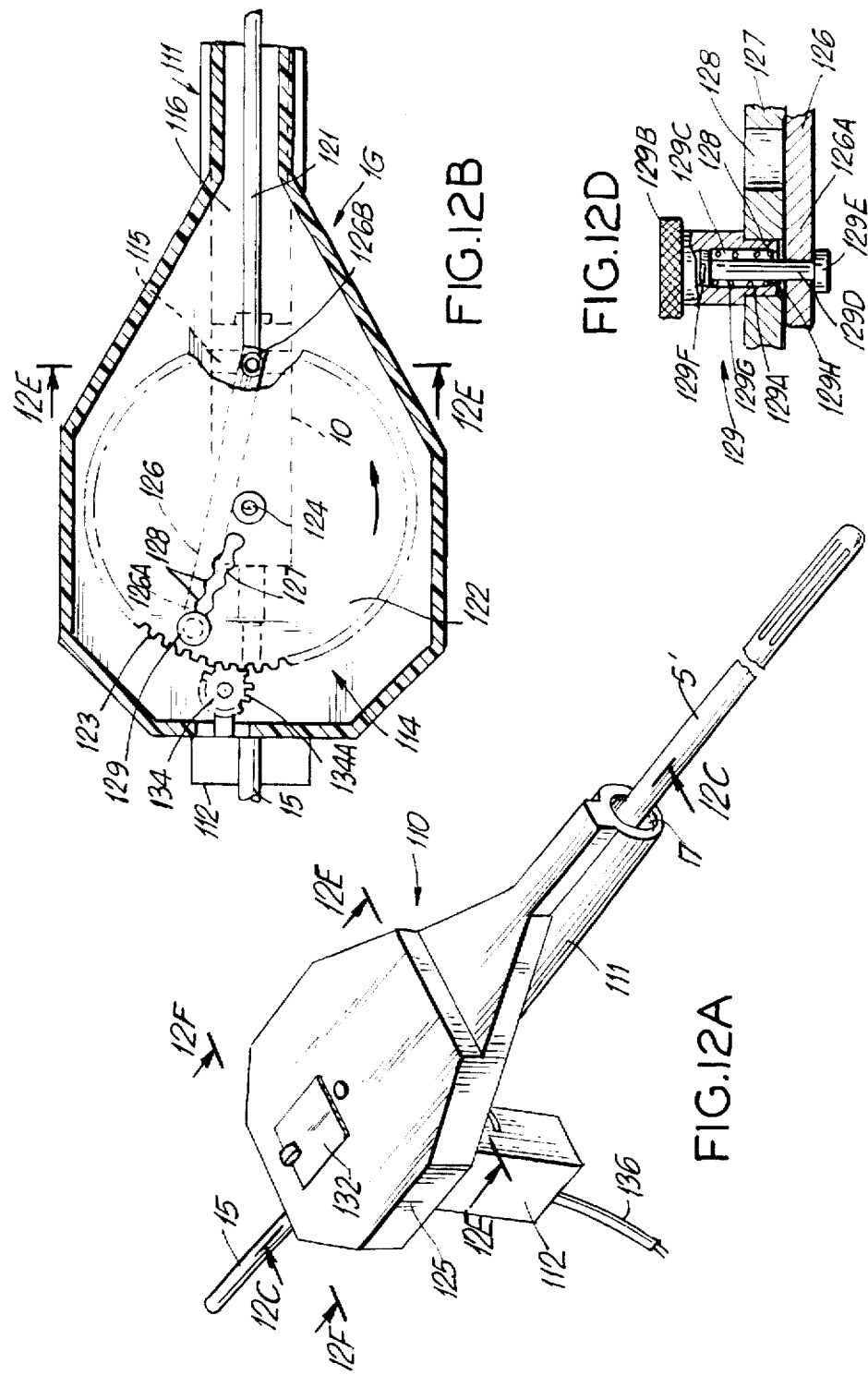

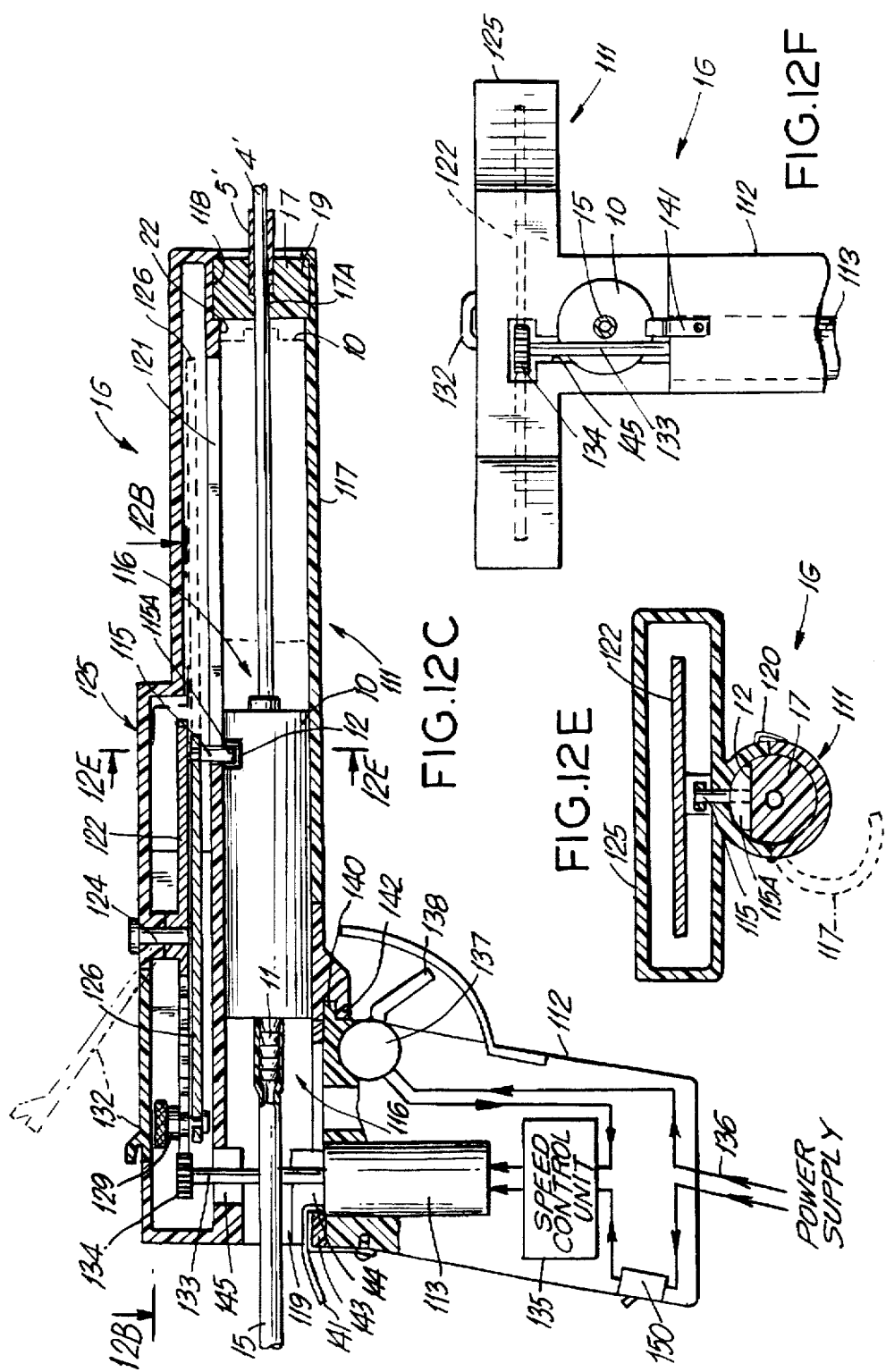

POWER-ASSISTED LIPOSUCTION INSTRUMENT AND CANNULA ASSEMBLY THEREFOR

This Application is a Continuation of application Ser. No. 08/307,000 filed Sept. 16, 1994, now U.S. Pat. No. 5,643,198 which is a Continuation application Ser. No. 07/627,240 filed Dec. 14, 1990, now U.S. Pat. No. 5,348,535.

FIELD OF INVENTION

The present invention relates generally to a method and apparatus for performing liposuction, and more particularly to a method and apparatus for performing liposuction in a mechanically assisted manner using powered expedients.

BRIEF DESCRIPTION OF THE PRIOR ART

Suction lipectomy, commonly known as liposuction or lipoxheresis, is a well known surgical procedure used for sculpturing or contouring the human body to increase the attractiveness of its form. In general, the procedure involves the use of a special type of curet known as a cannula, which is operably connected to a vacuum source. The cannula is inserted within a region of fatty tissue where removal thereof is desired, and the vacuum source suctions the fatty tissue through the suction aperture in the cannula and carries the aspirated fat away. Removal of fat cells by liposuction creates a desired contour that will retain its form.

Presently, there are two widely accepted techniques of liposuction and each may be practiced using a conventional liposuction cannula. The first and most common method proposed by Yves-Gérard Illouz and described in the paper "Illouz's Technique of Body Contouring by Lipolysis" in Vol. 3, No. 3, July 1984 of Clinics in Plastic Surgery, involves making regular tunnels at a depth of at least 1 centimeter under the skin. According to this method, one or two insertions are made, with radial excursions of the cannula into the fatty tissue of the patient. The result is a multitude of concomitant sinuses formed below the subcutaneous fatty tissue, leaving intact as far as possible the connections between the skin and underlying tissue, thereby retaining the blood vessels, the lymphatics and the nerve endings. The second method is the original liposuction procedure proposed by U. K. Kesselring, described in "Body Contouring with Suction Lipectomy", in Vol. 11, No. 3, July 1984, Clinics in Plastic Surgery. According to the technique, an entire layer of regular, deep fat is removed by aspiration through the cannula, leaving a smooth, deep surface of the residual panniculus. The space thus created is then compressed, optimally followed by skin retraction.

Both of these prior art liposuction techniques require that the surgeon push and pull the entire cannula back and forth almost twenty times for each insertion made. Typically, twenty to thirty tunnels are made. This is necessary to ensure even removal of fat in the targeted region. During this procedure, the surgeon typically massages the flesh in the area of the aperture in the cannula, while at the same time, thrusting the rod in and out of the tunnel. Due to the trauma involved during the procedure, the patients' skin turns black and blue for several weeks. Due to the physically exacting nature of the procedure, the surgeon typically comes out of an operating room extremely tired and suffers from muscular fatigue which prevents him from performing, for some time thereafter or the delicate operations involved in ordinary plastic surgery.

Recently, the use of a "guided cannula" has been proposed by R. de la Plaza, et al., described in "The Rationalization of Liposuction Toward a Safer and More Accurate Technique," published in Vol. 13, Aesthetic Plastic Surgery, 1989. According to the technique, a cannula is used in conjunction with an outer guide sheath through which the cannula can slidably pass while held in place by the handle portion of the guide sheath. Once the cannula and its sheath have been introduced into the fatty tissue, the sheath guide remains in the tunnel and guides successive introductions of the cannula, keeping it in the same tunnel. While the use of this liposuction technique offers some advantages over the conventional unguided liposuction cannulas, the guided cannula nevertheless suffers from several significant shortcomings and drawbacks. In particular, the guided cannula requires manually thrusting the cannula through the guide sleeve repeatedly for each tunnel. Although this is a less physically demanding procedure, the surgeon must thrust the cannula even more times through each tunnel to achieve the desired effect and hence is still easily fatigued and prevented him from performing, for some time thereafter, delicate operations involved in ordinary plastic surgery.

In an attempt to solve the above-described problem, U.S. Pat. Nos. 4,735,605, 4,775,365 and 4,792,327 to Swartz disclose an assisted lipectomy cannula having an aspiration aperture which effectively travels along a portion of the length of the cannula, thereby obviating the necessity of the surgeon to repeatedly push the cannula in and out of the patients' subcutaneous tissue where fatty tissue is to be removed. While this assisted lipectomy cannula can operate on either air or electric power, it nevertheless suffers from several significant shortcomings and drawbacks. In particular, the device requires an outer tube with an elongated slot and a inner tube having a spiral slot which must be rotated inside the outer tube to effectuate a traveling aspiration aperture. In addition to the devices overall construction posing difficulties in assembly, cleaning and sterilization, use with a variety of cannulas and highly effective fat aspiration does not appear possible.

Accordingly, there is a great need in the art for a mechanically assisted lipectomy cannula which overcomes the shortcomings and drawbacks of prior art lipectomy apparatus.

Thus, it is a primary object of the present invention to provide an improved method and apparatus for performing liposuction which assists the surgeon in the removal of fat and other subcutaneous tissue (such as but not restricted to gynecomastia) from surrounding tissue, with increased control and without promoting physical fatigue.

It is another object of the present invention to provide such apparatus in the form of a hand-holdable liposuction instrument having a cannula assembly, in which the location of the aspiration aperture is periodically displaced as the inner or outer cannulas undergoes sliding movement relative to the hand-holdable housing.

It is a further object to provide such a liposuction instrument in which the rate of reciprocation and the amount of excursion of the aspiration aperture, are selectively adjustable by the surgeon during the course of operation.

An even further object of the present invention is to provide such a liposuction instrument which can be driven by air or electricity.

A further object of the present invention is to provide such a liposuction instrument, in which the cannula assembly car be simply detached from the hand-holdable housing for ease of replacement and/or sterilization.

An even further object of the present invention is to provide an improved method of performing liposuction, in which one of the cannulas of the cannula assembly is automatically reciprocated back and forth relative to the hand-holdable housing, to permit increased control over the area of subcutaneous tissue where fatty and other soft tissue is to be aspirated.

These and other objects of the present invention will become apparent hereinafter.

SUMMARY OF INVENTION

According to one aspect of the present invention, there is provided apparatus for performing power-assisted liposuction. In general, the apparatus is realized as a device comprising a hand-holdable housing, a cannula assembly, and a reciprocation means.

The hand-holdable housing has a cavity adapted for receipt of a portion of the cannula assembly. The cannula assembly includes a hollow inner cannula and a hollow outer cannula. The hollow inner cannula has a distal end and a proximal end and at least one aspiration aperture disposed about the inner cannula distal end. The inner cannula proximal end includes an outlet port and a continuous passageway which communicates the inner aspiration aperture with the outlet port. A hollow outer cannula has a distal end and a proximal end and at least one outer suction aperture disposed about the outer cannula distal end. The hollow inner cannula is positionable within at least a portion of the hollow outer cannula so as to enable sliding movement between the hollow outer and inner cannulas while permitting aspiration through the outer and inner suction apertures, along said continuous passageway and out of the outlet port. The reciprocation means is disposed within the hand-holdable housing and is operably associated with either the hollow inner cannula or the hollow outer cannula, and the other of the inner and outer cannulas is essentially stationary with respect to the hand-holdable housing. In this way, relative sliding movement between the hollow inner and outer cannulas can be effectuated when the reciprocation means causes either the hollow inner or outer cannula to reciprocate, and thereby periodically displace the location of the aspiration through the outer and inner suction apertures.

In one embodiment, the inner cannula is stationarily disposed relative to the hand-holdable housing, and the outer cannula is operably associated with the reciprocation means to be selectively reciprocatable relative to the statuary inner cannula. In another embodiment, the outer cannula is stationarily disposed relative to the hand-holdable housing, and the inner cannula is operably associated with the reciprocation means to be selectively reciprocatable relative to the stationary outer cannula. In both embodiments, the effective aspiration aperture is periodically displaced along the distal end of cannula assembly.

Most significant of the present invention is that reciprocation of one of the cannulas is such that periodic displacement of the effective aspiration aperture of the cannula assembly is on the order of the length of tunnels formed in fatty tissue during the liposuction procedure. In order to achieve such magnitudes of reciprocation with a hand-holdable housing that fits into a surgeons hand, a number of constructions are disclosed. In general, one class of power-assisted liposuction devices according to the present invention is characterized by the placement of the cannula cavity within the hand-holdable housing so that the cannula cavity extends along the longitudinal extent of the hand-holdable housing. In this way, it is possible to effectuate displacement of the effective aspiration aperture by an amount on order of that achieved by manual reciprocation of a cannula during a conventional liposuction procedure. In certain embodiments, the cannula cavity advantageously extends along the entire longitudinal extent of the liposuction device housing.

In the illustrated embodiments, the cannula assembly is releasably detachable from the hand-holdable housing to facilitate cleaning and sterilization of the liposuction device.

In several embodiments, the reciprocation means is realized using gas driven piston-type motor, which causes the cannula to reciprocate relative to the hand-holdable housing and means are provided for controlling the amount of aspiration aperture excursion, as well as rate of aspiration aperture reciprocation.

In another embodiment, a pair of gas-driven piston-type motors are used to realize the reciprocation means. A mechanically-operated gas flow control device is provided for automatically controlling the flow of gas to effectuate reciprocation of the aspiration aperture.

In yet another embodiment, the hand-holdable housing is realized in the form of a pistol, having a barrel portion and a handle portion, facilitating the use of a rotary type motor without compromising desired amounts of aspiration aperture excursion.

As a result of the present invention, aspiration of fat and other soft tissue can be achieved with a light-weight, hand-holdable instrument, that eliminates fatigue of the surgeon. The simplified mechanical construction of the instruments of the present invention provides improved performance and simplified cleaning, sterilization, and maintenance.

BRIEF DESCRIPTION OF THE DRAWINGS

For a fuller understanding of the objects of the present invention, reference is made to the detailed description of the illustrative embodiments which are to be taken in connection with the accompanying drawings, wherein:

FIG. 1A is a perspective view of a first embodiment of the liposuction device of the present invention;

FIG. 1B is a cross-sectional view of the liposuction device of the present invention taken along line 1B—1B of FIG. 1A;

FIG. 1C is an elevated end view of the liposuction device of the present invention illustrated in FIG. 1A, showing the cannula assembly retained within the cannula cavity of the hand-holdable housing, and alternatively with the hingedly connected housing cover panel disposed in an open position for removal of the cannula therefrom;

FIG. 2A is a perspective, partially broken away view of the cannula assembly installed in the liposuction instrument of FIGS. 1A through 1C, in which the reciprocatable inner cannula has projections which pass through and extend above elongated apertures in the stationary outer cannula;

FIG. 2B is a perspective view of the distal end of the inner cannula shown in FIGS. 1A, 1B and 2A;

FIG. 2C is a cross-sectional view of the inner cannula taken along line 2C—2C of FIG. 2B;

FIG. 2D is a perspective, partially broken away view of the outer cannula shown in FIGS. 1A, 1B and 2A;

FIG. 3A is a perspective, partially broken away view of an alternative cannula assembly for use with the liposuction instrument shown in FIGS. 1A through 1C, in which the inner cannula is adapted to freely undergo sliding movement within the stationary outer cannula;

FIG. 3B is a perspective, partially broken away view of the distal end portion of the inner cannula shown in FIG. 3A;

FIG. 3C is a cross-sectional view of the inner cannula taken along line 3C—3C of FIG. 3B;

FIG. 3D is a perspective, partially broken away view of the outer cannula shown in FIG. 3A;

FIG. 3E is a cross-sectional view of the cannula assembly taken along line 3E—3E of FIG. 3A;

FIG. 6A is a cross-sectional, partially broken away view of a fourth embodiment of the liposuction device of the present invention;

FIG. 6B is a perspective, partially broken away view of the distal end portion of the cannula assembly shown in FIG. 6A, in which the reciprocatable outer cannula has projections which extend above elongated apertures formed in the stationary inner cannula;

FIG. 6C is a cross-sectional view of the cannula assembly taken along line 6C—6C of FIG. 6B;

FIG. 6D is a cross-sectional view of the cannula assembly taken long line 6D—6D of FIG. 6B, showing a keying element extending into one of the elongated apertures to prevent relative rotation between the inner and outer cannulas;

FIG. 6E is a cross-sectional view of another embodiment of the cannula assembly shown in FIG. 6A, in which the outer cannula has a surface contour with continuously formed circumferentially spaced projections, about which are aspiration apertures through which aspiration of fatty tissue can occur;

FIG. 7 is a cross-sectional partially broken away view of a fifth embodiment of the liposuction device of the present invention, illustrating an alternative inner and outer cannula retention means;

FIG. 8A is a perspective, partially broken away view of an alternative cannula assembly adapted for use with the liposuction instrument shown in FIGS. 1A through 1C, in which the reciprocatable inner cannula is free to slidably move within the stationary outer cannula;

FIG. 8B is a perspective view of the distal end of the inner cannula shown in FIG. 8A;

FIG. 8C is a cross-sectional view of the cannula assembly taken along line 8C—8C of FIG. 8B;

FIG. 8D is a cross-section view of the cannula assembly taken along line 8D—8D of FIG. 8B;

FIG. 9A is cross-sectional view of a sixth embodiment of the liposuction device of the present invention, illustrating the use of a pair of gas driven piston-type motors and a mechanically-operated gas flow control device disposed in its first state of operation;

FIG. 9B is a cross-sectional view of the liposuction device of the present invention taken along line 9B—9B of FIG. 9A;

FIG. 9C is a perspective view of the preferred embodiment of the mechanically-operated gas flow control device illustrated in FIG. 9A;

FIG. 9D is a cross-sectional view of the gas flow control device of the present invention taken along line 9D—9D of FIG. 9C.

FIG. 10A is a perspective, partially broken away view of a snap-fit type inner cannula intended for use with the second embodiment of the liposuction device of the present invention;

FIG. 10B is a cross-sectional view of the outer cannula of the present invention taken along lines 10B—10B of FIG. 10A;

FIG. 11 is a perspective, partially broken away view of a snap-fit type outer cannula intended for use in connection with the second embodiment of the liposuction device of the present invention;

FIG. 12A is a plan cross-sectional view of a seventh embodiment of the liposuction device of the present invention, having a hand-holdable housing realized in the form of a pistol-shaped structure having detachable barrel and handle portions;

FIG. 12B is a cross-sectional, partially broken away view of the liposuction device of the present invention taken along line 12A–12B of FIG. 12A, showing the cam mechanism of the present invention;

FIG. 12C is an elevated cross-sectional view of the liposuction device of the present invention, taken along line 12C—12C of FIG. 12A, showing the inner cannula disposed at a first position within the cannula cavity of the hand-holdable housing, and the rotary motor and speed control unit in the handle portion thereof;

FIG. 12D is a cross-sectional view of a portion of the inner cannula excursion control means shown in FIGS. 12B and 12C;

FIG. 12E is a cross-sectional view of the liposuction device of the present invention taken along line 12E—12E of FIG. 12A, showing the rotary drive wheel of the cam mechanism in operable association with the actuation element which projects through the cannula cavity and is engaged in the slotted base portion of the inner cannula, and also showing in phantom lines the cover panel of the barrel portion disposed in an open configuration permitting insertion or removal of the inner and outer cannulas of the present invention; and FIG. 12F is an elevated partially broken away rear view of the barrel portion of the liposuction device taken along line 12F—12F of FIG. 12A.

DETAILED DESCRIPTION OF THE ILLUSTRATED EMBODIMENTS

Figure 4A:
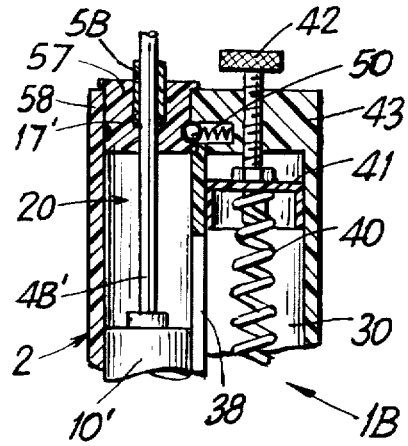
FIG. 4A is a cross-sectional view of a portion of a second embodiment of the liposuction device of the present invention, illustrating an alternative outer cannula retention means.

With reference to FIGS. 1A through 3D, the first embodiment of the liposuction device of the present invention will be described. In general, liposuction device 1A comprises a hand-holdable housing 2, a detachable cannula assembly 3 having inner and outer cannulas 4 and 5, and a reciprocation means 6 for causing inner cannula 4 to reciprocate relative to outer cannula 5, which is stationarily disposed with respect to housing 2. This arrangement effectuates periodic displacement of the general location of aspiration along the cannula assembly through the reciprocating movement of inner cannula 4.

As illustrated in greater detail in FIGS. 1B, and 2A through 2E, outer cannula 5 comprises a hollow outer tube having a distal end 4C of inner cannula 4, 5A and a proximal end 5B. At the distal end, three projections 7A, 7B and 7C are provided above a respective inner aspiration (i.e., suction) aperture generally indicated by reference numerals 8A, 8B and 8C. As shown in FIG. 2C, the accurately shaped projections of this embodiment are arranged in a T-configuration, and bridge distal tip portion 4C and portion 4D between which a continuous aspiration opening 9 originates below the projections and extends through the entire length of the inner tube. By the nature of this construction, aspiration apertures 8A, 8B and 8C each merge into continuous opening 9. Projections 7A and 7C are also diametrically disposed, with projection 7B disposed therebetween. Preferably, these projections have a resilient nature and are capable of being temporarily collapsed under predetermined loading during assembly, which, however, is not typically experienced during normal liposuction procedures.

Extending from the proximal end of inner cannula 4 is an inner cannula base 10 comprising a cylindrical structure having an outlet port 11 formed in its remote end. As illustrated in FIG. 1B, inner cannula base 10 includes a notch or slot 12 formed in its central most portion. As will be described in greater detail hereinafter, notch 12 functions to releasably receive an extensional portion 13 of actuation element 37, in order to actuate reciprocation of inner cannula 4 within housing 2. As illustrated in FIG. 2B, inner cannula 4 has a continuous passageway 14 which extends from inner aspiration opening 9 to outlet port 11. While not shown, a conventional vacuum source is connected to outlet port 11, preferably using optically transparent, semi-flexible tubing 15. With this arrangement, fatty tissue, aspirated through apertures 8A, 8B and 8C and opening 9, can be transported through passageway 14 to a reservoir device (not shown), operably associated with the vacuum source.

As illustrated in FIG. 2D, outer cannula 5 comprises a hollow outer tube having a distal end 5A and a proximal end 5B. At the distal end, elongated aspiration (i.e., suction) apertures 16A, 16B and 16C are formed. The arrangement of these apertures is such that projections 7A, 7B and 7C from inner cannula 4 extend through and are free to slide within these elongated apertures, as shown in FIGS. 1B and 2A. As shown, elongated apertures 16A, 16B and 16C terminate at a predetermined distance away from outer cannula tip 5C, which is essentially blunt for purposes of safety. In general, the length of each of these elongated apertures is substantially longer than the longitudinal extent of each respective projection. In the illustrated embodiment, the ratio of these lengths is about 1 to 4; however, in other embodiments, this ratio may differ as desired or required in a given application. In a typical embodiment, the length of these elongated apertures would be within the range of, for example, two to six inches, commensurate with the amount of displacement to be achieved by each projection.

Extending from the proximal end of outer tube 5 is an outer cannula base 17 comprising a cylindrical structure having a central bore 18, through which distal tip 4C and body of inner cannula 4 can freely pass. As illustrated in FIG. 1B, outer cannula base 17 of this embodiment includes a flanged portion 19 which fits within an annular recess formed in cannula cavity 20 of the hand-holdable housing.

Since projections 7A, 7B and 7C of the illustrated embodiment have resilient, spring-like characteristics and yield (i.e., compress) when subjected to a predetermined load, they temporarily collapse when pushed through bore 18 in the outer cannula base. Consequently, these temporarily collapsed projections will subsequently re-erect themselves upon aligning with and projecting through respective elongated apertures 16A, 16B and 16C in outer cannula 5. When inner cannula 4 is installed within outer cannula 5, as shown in FIGS. 1A and 2A, projections 7A, 7B and 7C are free to slide along apertures 16A, 16B and 16C, respectively. Also, at each positioning of the inner cannula within the outer cannula, aspiration is permitted through each "effective" aspiration (i.e., suction) aperture formed by the partial registration of each outer aspiration aperture 16A, 16B and 16C with inner aspiration aperture 9, formed below its respective projection. Aspiration through these resulting effective aspiration apertures or openings, continues along passageway 14 and exits through outlet port 11. Consequently, the general location of aspiration along cannula assembly 3 is periodically displaced as inner cannula 4 is reciprocated relative to outer cannula 5, which is stationary with respect to housing 2.

In FIGS. 3A through 3D, an alternative cannula assembly is shown for use with liposuction devices of FIGS. 1A through 1C, 4A and 4B, respectively. Cannula assembly 3' comprises inner cannula 4' and outer cannula 5', each comprising hollow inner and outer tubes with distal and proximal ends 4A', 4B' and 5A', 5B', respectively. As shown, inner cannula 4' also includes inner cannula base 10 described above, whereas outer cannula 5' includes outer cannula base 17, also described above. Outer cannula 5' has elongated aspiration apertures 16A, 16B and 16C which extend along the longitudinal extent of outer cannula tube 5. Inner tube 4', on the other hand, has three circumferentially spaced-apart aspiration apertures 8A', 8B' and 8C'. FIG. 3B which are axially aligned with apertures 16A, 16B and 16C, respectively, when inner cannula 4' is slidably inserted into outer cannula 5'. In order to maintain inner aspiration apertures 8A', 8B' and 8C' aligned with outer aspiration apertures 16A, 16B and 16C, respectively, and thus ensure partial registration therebetween, the distal end of inner cannula 4' is provided with a keying system. In the illustrated embodiment, the keying system comprises a keying element 4D' disposed on outer cannula surface before distal tip 4A'. Keying element 4D' slides within elongated aperture 8B' and prevents axial rotation between cannulas 4' and 5 as they undergo relative reciprocation.

To assemble cannula assembly 3', distal tip 4A' of the inner cannula is inserted through bore 18 in outer cannula base 17 so that the distal end of inner cannula 4' is slidably received within outer cannula 5', as shown in FIG. 3A. In this configuration, keying element 4D' is received and guided within elongated aperture 8B' as shown. In this general configuration, cannula assembly 3' is installed within cannula cavity 20 by first opening housing cover 21, shown in FIG. 1C. Then outer cannula base flange 17 is inserted within annular recess 19 and actuation extension 13 within inner cannula base notch 12. Thereafter, housing cover 21 is closed shut and liposuction device 1A is ready for operation.

A variety of outer cannulas for the above-described cannula assembly is contemplated. For example, reciprocatable outer cannulas with projections having cutting and non-cutting surfaces are contemplated for fat or gynecomastia. Also, reciprocatable outer cannulas having small diameters and small outer aspiration apertures are contemplated for facial and submental liposuction. For abdomen and extremities, reciprocatable outer cannulas with large aspiration apertures are contemplated.

As shown in FIG. 1A, the gross geometry of housing 2 is preferably that of an ellipsoid, however, other geometries such, for example, as a cylindrical structure, can be used in practicing the present invention. Housing 2 contain cannula cavity 20, which extends along the entire longitudinal extent of the hand-holdable housing. In the illustrated embodiment, cannula cavity 20 has generally cylindrical bearing surfaces 22 which match the outer bearing surface 23 of inner cannula base 10, to permit sliding movement of inner cannula 3 within cavity 20. While cylindrical bearing surfaces have been selected in the illustrated embodiment, use of other forms of bearing surfaces (e.g., rectangular or triangular) are contemplated. To minimize friction, bearing surfaces 22 and 23 may be coated with a Teflon® or functionally equivalent coating, to facilitate easy sliding of inner cannula base 10 within cavity 20 with low wear. As illustrated in FIG. 1B, cannula cavity 20 also includes annular recess 19, into which annular base flange 19 is adapted to be received in order to render the outer cannula essentially stationary with respect to hand-holdable housing 2.

As illustrated in FIG. 1C, hand-holdable housing 2 is provided with a hinged cover 21. Hinged cover 21 allows cannula cavity 20 to be opened and accessed so that cannula assembly 3 can be selectively installed in cannula cavity 20 and removed therefrom as desired or required. Cover panel 21 has a semi-circular cross-sectional geometry and is connected to the remaining portion of housing 2 by a conventional hinge means 25. To secure cover panel 21 to the remainder of housing 2, a releasable locking means 26 is provided at the interface of hinge cover 21 and housing 2, as shown. Releasable locking means 26 can be realized in a variety of ways, including, for example, using a spring biased clamp element 27 which engages in a notch 28 formed in the external surface of the remaining housing portion, as illustrated in FIG. 1C.

To effectuate reciprocation of inner cannula 4 within cannula cavity 20 and thus within stationary outer cannula 5, a gas or electrically driven motor(s) can be used to realize reciprocation means 6 of present invention. In the embodiments illustrated in FIGS. 1A through 1C, 4A through 6A, 7 through 8A, and 9A through 9D, one or more gas driven piston-type motors are employed. In the embodiment illustrated in FIGS. 12A through 12F, a rotary-type motor is used to realize reciprocation means 6 of the present invention.

As illustrated in FIG. 1B, a piston-type motor 6 is mounted within a motor cavity 30 provided adjacent cannula cavity 20 of housing 2. Notably, this reciprocation means cavity 30 extends essentially parallel to cannula cavity 20 and along a substantial portion of the longitudinal dimension of hand-holdable housing as will become more apparent hereinafter. This unique spatial relationship between the cannula cavity and reciprocation means cavity within housing 20, ensures optional cannula displacement relative to longitudinal dimensions of the hand-holdable housing.

In general, motor 6 comprises a chamber housing 31 having a gas inlet port 32 and an inner chamber generally indicated by reference numeral 33. Slidably received within the inner chamber of housing 31 is a movable piston 34 having formed in the lower portion wall 35, one or more gas outlet ports 36. Mounted to the top portion of movable piston 34, is actuation element 37, whose extension 13 projects through longitudinally disposed slot 38 formed in the bearing wall surface 22 of cannula cavity 20. As shown in FIG. 1B, actuation extension 13 passing through slot 38, is received within notch 12 formed in inner cannula base 10 and operably associates inner cannula 3 with motor 6.

As illustrated in FIG. 1B, chamber housing 31 is fixedly disposed within motor cavity 30. Motor cavity 30 is also provided with at least one port 39 for ventilating to the ambient environment, gas released from inner chamber 33 upon movable piston 34 reaching it maximum displacement or excursion. Movable piston 34 is biased in the direction of chamber housing 31 by way of a spring biasing element 40. The compliance of spring biasing element 40 can be adjusted by moving the position of slidable wall 41 by rotating, for example, threaded element 42 passing through a portion 43 of housing 2, as shown. With this arrangement, adjustment of wall 41, closer to or farther from chamber housing 31, results in decreasing or increasing, respectively, the compliance of spring biasing element 40. This mechanism, in turn, provides a simple, yet reliable way in which to control the rate of reciprocation of movable piston 34, and thus the rate of reciprocation of inner cannula 3 relative to housing 2.

The manner of operation of piston-type motor 6 is described as follows. Gas, such as pressurized air or $N_2$ gas, is introduced under constant pressure to inlet port 32 of chamber housing 31. As the gas fills up the volume enclosed by the interior walls of movable piston 34 and chamber 33, inner chamber 33 begins to expand, forcing movable piston 34 upwardly against the biasing force of spring biasing element 40. When movable piston 34 is displaced sufficiently enough from chamber housing 31 so that gas within expanding chamber 33 can be released through gas exit port 39 to the ambient atmosphere, piston 34 will be forced back downwardly into chamber housing 31. The rate of the forced downward piston movement is inversely proportional to the compliance of spring biasing element 40. Subsequently, chamber 33 will again fill up with gas, piston 34 will again be displaced and gas subsequently vented, whereupon reciprocating displacement of piston 34 will be repeated again in a cyclical manner. Since movable piston 34 is operably connected with inner cannula base 10 by way of actuation element 37, this reciprocating movement of piston 34 results in reciprocating movement of inner cannula 3 within cannula cavity 20. Further, this relative reciprocation between the inner cannula and the outer cannula results in periodic displacement of the effective aspiration apertures along the distal end portion of the cannula assembly.

As illustrated in FIG. 1B, the amount of excursion that piston 34 is permitted to undergo before gas venting and subsequent downward piston movement occurs, is determined by the distance "d" defined between gas output port 32 and top wall surface 47 of chamber housing 31. A typical cannula excursion distance of about four inches, for example, will necessitate that the parameter d, defined above, be also about four inches.

Figure 4B:
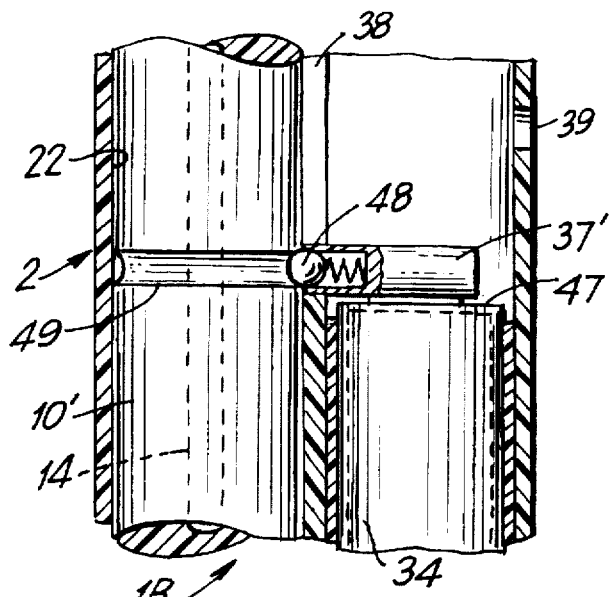
FIG. 4B is a cross-sectional view of another portion of a second embodiment of the liposuction device of the present invention, illustrating an alternative inner cannula retention means.

In FIGS. 4A and 4B, a second embodiment of the liposuction device of the present invention is shown. Liposuction device 1B has an alternative cannula assembly retention means while inhering all of the structural features of the first embodiment illustrated in FIGS. 1A through 1C. In particular, the liposuction device 1B illustrated din FIG. 4A and 4B does not have a hingedly connected housing cover panel, and instead incorporates a snap-fit type cannula assembly retention mechanism. In accordance with this embodiment, actuation element 37' has an extension which is essentially flush with an elongated slot 38 formed in cavity wall 22. As shown in FIG. 4B, this extension is provided with a spring biased ball bearing 48 that projects slightly beyond cannula cavity wall surface 22. When inner cannula base 10' is pushed into cannula cavity 20 in the vicinity of actuation element 37', ball bearing 48 engages within an indentation ring 49 circumferentially formed about inner cannula base 10'. Notably, spring biased ball bearing 48 functions as an engaging means for inner cannula base 10'.

Similarly, as shown in FIG. 4A, an engaging means for outer cannula base 17' is also realized as a spring biased ball bearing 50 installed through cannula cavity wall 22. Outer cannula base 5' is provided with an annular flange 47 and indentation ring 49 circumferentially formed about outer cannula base 17'. As shown, annular flange 57 establishes surface to surface contact with peripheral surface 58 area of the housing when cannula base 5' is pushed into cannula cavity 20. In this position, ball bearing 50 engages within indentation ring 49 and a snap-fit engagement is established. This arrangement serves to retain both the inner and outer cannulas in cannula cavity 20, in a releasable manner, as actuation element 37' is caused to reciprocate periodically. The outer cannula is simply removed from cannula cavity 20 by quickly pulling on the outer cannula with a modest degree of force, to overcome the bias force of engaged ball bearing 50. Similarly, the inner cannula is simply removed by quickly pulling on the inner cannula the to overcome bias force of engaged ball bearing 50. Advantageously, this cannula assembly retention mechanism can also provide a safety release feature, in that if the inner cannula, for example, becomes snagged during an operation, it will disengage from the reciprocation means if a proper spring biasing force is selected for ball bearing 50.

FIGS. 10A, 10B and 11 also show inner and outer cannulas adapted for use with liposuction instruments having cannula retention capabilities of the snap-in type described above. Notably, the elements which correspond to inner and outer cannulas illustrated in FIGS. 2A through 2D and 3A through 3E, are indicated by similar reference numbers.

In the embodiment featured in FIGS. 10A and 10B, inner cannula base 10" has a deeply formed spherical indentation 52 which is adapted to receive ball bearing 48 mounted in the extension of in actuation element 37. To facilitate guiding ball bearing 48 into spherical indentation 52, a longitudinally extending groove 53 is formed in inner cannula base 10". Also, as shown, widened recess portions 53A and 53B are provided at opposite ends of groove 53 to facilitate initial insertion of ball bearing 48 in groove 53. When inner cannula base 10" is slid into cannula cavity 20, ball bearing 48 snaps into indentation 52 to establish a locked position. Biased ball bearing 48 engaged in spherical indentation 52 serves to retain inner cannula 5 within cannula cavity 20, while facilitating reciprocation of inner cannula 5 when actuation element 37' is caused to reciprocate.

Similar to the snap-fit inner cannula retention mechanism illustrated in FIGS. 10A and 10B, FIG. 11 shows outer cannula base 17' having a longitudinally extending groove 55. Also, as shown, widened recess portions 55A and 55B are formed at opposite ends of groove 55 to facilitate insertion of ball bearing 50 into spherical indentation 56. When outer cannula base 17' is slid into cannula cavity 20, ball bearing 50 snaps into spherical indentation 56 to establish a locked position. When this occurs, annular flange 57 will engage with outer peripheral surface 58, about circular access opening leading into cannula cavity, shown in FIG. 4A. Upon such engagement, outer cannula 5 is rendered stationary relative to hand-holdable housing 2. As with inner cannula 4, the outer cannula is simply removed from cannula cavity 20 by pulling on outer cannula tube 5 with a modest degree of force to overcome the bias force of engaged ball bearing 50.

Figure 5:
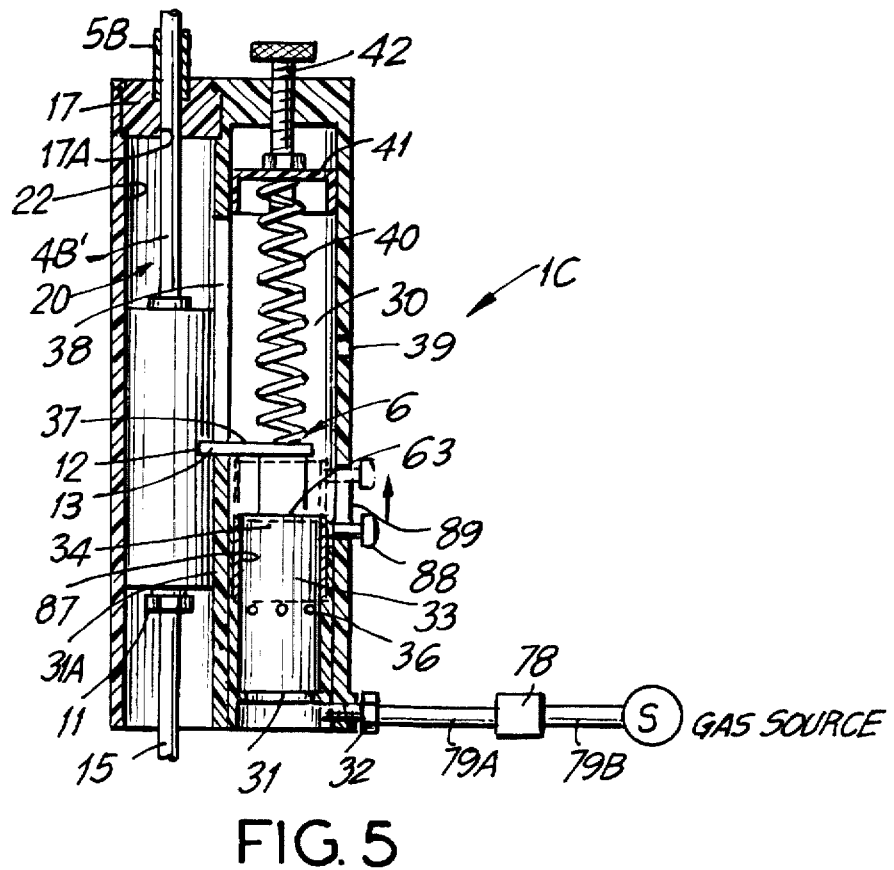
FIG. 5 is a cross-sectional view of a third embodiment of the liposuction device of the present invention, illustrating a means for controlling the amount of excursion of the aspiration aperture along the cannula assembly.

In order to selectively adjust the amount of cannula excursion permitted during a liposuction operation, piston-type motor 6 can be modified, as shown in FIG. 5, to produce a third embodiment of the liposuction device of the present invention. As illustrated in FIG. 5, the basic structure of liposuction device 1C is similar to that shown in FIGS. 1A through 1C, except that a user-adjustable intermediate housing wall 88 is disposed between the inner walls 31A of chamber housing 31 and the outer walls 34A of movable piston 34. Intermediate housing wall 87 is operably associated with an excursion selection means realized as a slidable member 88 fixedly attached to the upper portion of intermediate housing wall 59. Preferably, slidable member 88 extends through a slot 89 formed in the wall of housing 2 and can be slid, for example, by movement of the surgeon's thumb. The function of intermediate housing wall 87 is to effectively raise the height of the chamber housing wall, and thus selectively increase distance d, defined, for example, as the distance between gas outlet port 32 in piston 34 and upper portion 63 of the chamber housing wall. In this way, movable piston 34 must undergo a larger displacement before compressed gas will be released and piston 34 permitted to be forced downwardly under the biasing force of biasing spring element 40.

As illustrated in the embodiment shown in FIG. 5, it is also possible to control the rate of reciprocation of the inner cannula by controlling the rate of gas flow entering chamber 33 of piston-type motor 6. This can be achieved using a conventional gas flow regulation device 78 inserted between source of gas "S" and inlet port 32 of chamber housing 31. As shown, tubing sections 79A and 79B are used to achieve fluid communication between these elements. Typically, cannula reciprocation rates will be in the range of 30 to 90 reciprocation cycles per minute, and the corresponding gas flow rates will depend on parameters including, for example, the compliance of biasing spring 40, the volumes of movable piston 34 and chamber housing 31, the cross-sectional diameter of gas inlet port 32, and the cross-sectional diameter of gas outlet ports 36 in the piston.

Referring to FIGS. 6A through 6E, there is shown a fourth embodiment of the liposuction device of the present invention. In this embodiment corresponding elements will be designated with same reference numerals. In liposuction device 1D, housing 2 and reciprocation means 6 are generally similar to those of the previously described embodiments. Cannula assembly 3" is different, however, in significant respects from that of the previously described embodiments. In liposuction device 1D, cannula assembly 3" comprises an inner cannula 4" stationary relative to housing 2, and an outer cannula sleeve 5" disposed over the inner cannula and reciprocatable therealong by operably associated reciprocation means 6.

As illustrated in FIGS. 6A and 6B, inner cannula 4" comprises a hollow tube having a distal end 4A" and proximal end 4B". Hollow inner tube 4" has three elongated aspiration apertures 60A, 60B and 60C formed along the distal end, as shown. Extending from the proximal end, there is an inner cannula base 61 comprising a cylindrically shaped structure with central passageway 62 and outlet port 63. Elongated aspiration apertures 60A, 60B and 60C are in communication with central passageway 62 so as to permit aspiration of fatty tissue through these apertures, along hollow tube 4" and out of outlet port 63. In order to retain inner cannula 4" stationarily positioned relative to housing 2, inner cannula base 61 is provided with an annular flange 64 which is releasably received within a matching annular recess 65 formed in the rear most portion of cannula cavity 20, as shown.

As illustrated in FIGS. 6A and 6B, outer cannula 5" comprises a hollow outer tube (i.e., sleeve) having a distal end 5A" and a proximal end 5B". At the distal end, three circumferentially spaced-apart, elongated aspiration apertures 67A, 67B and 67C are formed longitudinally in outer sleeve 5", as shown. Extending above each elongated aperture 67A, 67B and 67C is an arcuately shaped projection, 68A, 68B and 68C, respectively. On the sides of each projection are passageways leading through the respective aspiration aperture. Preferably, the maximum height of each projection is approximately equal to the diameter of hollow outer sleeve 5". Extending from proximal end 5B", there is an outer cannula base 69 comprising a cylindrically shaped structure with a central disposed bore 70, through which inner cannula tube 4" can freely pass. In order to periodically displace outer cannula base 69 along cannula cavity 20, a notch 71 is formed in cylindrical outer base 69, into which actuation extension 13 can releasably engage, as shown in FIG. 6A.

When cannula assembly 3" is assembled, inner cannula 4" is inserted within hollow sleeve 5" and each outer aspiration aperture 67A, 67B and 67C is in at least partial registration with respective elongated inner aspiration apertures 60A, 60B and 60C. As illustrated in FIG. 6A, in this configuration, inner cannula base 61 is stationarily connected within cannula cavity 20, and outer cannula base 69 is engaged with actuation extension 13 and thus is operably associated with reciprocatable motor 6. As illustrated in FIG. 6D, distal tip portion 5C" of outer cannula sleeve 5" is provided a keying element 73 which extends radially inward and slides within elongated aperture 60B formed in the wall of inner cannula tube 4A". This keying system prevents the outer cannula sleeve 5" from axial misalignment as it undergoes reciprocating movement along inner cannula 4". In such a configuration, when motor 6 reciprocates, outer cannula sleeve 5" is slidably moved along inner cannula 4" so that the general location of aspiration through the partially registered aspiration apertures, is periodically displaced. At the same time, projections 68A, 68B and 68C above outer aspiration apertures 67A, 67B and 67C, respectively, are slidably moved about respective elongated inner aspiration apertures 60A, 60B and 60C.

In FIG. 6E, an alternative embodiment of distal portion 5A" of outer cannula sleeve 5" is illustrated. Therein, outer sleeve portion 5A"" comprises a surface contour in which projections 75A, 75B and 75C are continuously formed and circumferentially spaced about outer sleeve 5B". Also shown are pairs of aspiration apertures 76 formed in the side walls 77 of each projection. These apertures provide openings through which fatty tissue can be aspired and passed through inner aspiration aperture and along hollow inner tube. Advantageously, the essentially continuous surface contours of these projections and aspiration apertures provide reduction in resistance of outer cannula reciprocational movement through tunnels of fatty tissue formed during a liposuction procedure. At the same time, the projections can serve to (i) hold the layers of fatty tissue away from the underlying inner aspiration apertures 60A, 60B and 60C formed in the inner cannula, and/or (ii) facilitate dissection of fatty tissue to be aspirated.

In FIG. 7, a fifth embodiment of the liposuction device of the present invention as shown. Liposuction device 1E has an alternative cannula assembly retention means while inhering all of the structural features of the fourth embodiment illustrated in FIGS. 6A through 6E. In particular, liposuction device 1E does not have a hingedly connected cover panel, and instead has a cannula cavity that permits use of snap-fit type cannula assembly components, illustrated for example in FIGS. 4A and 4B. The extension of actuation element 37' projects essentially flush with elongated slot 38 in cavity wall 22. As show, this extension is provided with a spring-biased ball bearing 80 which projects slightly beyond cannula cavity wall surface 22, and engages within indentation ring 81, circumferentially disposed about outer cannula base 69. In this structural arrangement, spring biased ball bearing 80 functions as an engaging means for outer cannula base 69. Outer cannula 5B" is retained within cannula cavity 20 as actuation element 37' is caused to reciprocate. Similarly, an engaging means for inner cannula base 61 is also realized as a spring biased ball bearing 82, is installed through cannula cavity wall 22. As shown, ball bearing 82 engages with indentation ring 83, circumferentially disposed about inner cannula base 61. This structural arrangement serves to retain inner cannula 4" stationarily within cannula cavity 20 during operation of liposuction device 1E. As discussed in connection with liposuction device 1D of FIGS. 4A and 4B, the cannula bases of the inner and outer cannulas, shown in FIGS. 10A and 10B, can also be adapted for use as inner and outer cannula bases for the cannula assembly utilized in liposuction device 1E of FIG. 7.

In FIGS. 8A through 8C, an alternative cannula assembly is shown for use with the liposuction device of FIGS. 6A and 7 alike. Cannula assembly 3'" of the illustrated embodiment includes an inner cannula and an outer cannula comprising hollow inner and outer tubes 4'" and 5'", respectively. As shown, inner cannula 4'" also includes inner cannula base 61 as described above, whereas outer cannula 5'" includes outer cannula base 69, also described above. Inner tube 4'" has three circumferentially spaced apart, elongated aspiration apertures 60A, 60B and 60C which extend along the longitudinal extent of the distal end 4A'" of inner cannula tube 4'", as shown. Outer sleeve 5'", on the other hand, has three circumferentially spaced apart aspiration apertures 67A, 67B and 67C. As in the previous embodiment of FIGS. 6A through 6C, these aspiration apertures are axially aligned with elongated apertures 60A, 60B and 60C, respectively, that is, when inner cannula 4'" is slidably inserted into outer cannula 5'". In order to maintain aspiration apertures 60A, 60B and 67C aligned with respective aspiration apertures 67A, 67B and 67C, respectively, and thus ensure partial registration therebetween as outer sleeve 5'" is caused to reciprocate, distal end 5A'" of outer sleeve 5'" is provided with a keying system. In the illustrated embodiment shown in FIG. 8D, the keying system comprises keying element 73 which extends radially inward and slides within elongated aperture 60B, thereby preventing axial rotation between the cannulas as they are under relative reciprocation during liposuction instrument operation.

Assembly of cannula assembly 3" is similar to that of cannula assembly 3" shown in FIGS. 3A through 3D. For example, distal tip 4C'" of inner cannula 4'" is inserted through bore 70 in outer cannula base 69 so that distal end 4A'" of inner cannula 4'" is slidably received within outer cannula sleeve 5'" and extends therebeyond, as shown in FIG. 8B. In this configuration, keying element 73 is received and guided within elongated aperture 60B as shown in FIG. 8D. In this general configuration, cannula assembly 3'" is installed within cannula cavity 20 by first opening hinged cover panel which provides access to the interior of cannula cavity 20. Then inner cannula base flange 64 is inserted within annular recess 65 and actuation extension 13 within outer cannula base notch 71. Thereafter, the housing cover panel is closed shut and liposuction device 1E is ready for operation.

The components of cannula assemblies 3, 3', 3" and 3'" and other embodiments of cannula assemblies of the present invention can be made of a variety of materials, including, for example, stainless steel and plastic. Stainless steel offers the advantage of being easily cleaned and sterilizable, while plastic offers the advantage of low manufacturing cost and disposability. Preferably, when making the cannula from a suitable plastic material, injection molding processes can be used to form integrally molded inner cannulas and integrally molded outer cannulas, each having desired characteristics. The molded cannulas would be subsequently sterilized and packaged together. It is expected that in certain applications it may be desirable to form one of the cannulas from plastic material, and the other cannula from metal. In the surgical environment, the surgeon can simply remove a selected cannula assembly from its sterilized package, and insert the cannula assembly into the cannula cavity of a liposuction device of the present invention.

Referring to FIGS. 9A through 9D, there is shown a sixth embodiment of the liposuction device of the present invention. In liposuction device 1F, the housing and cannula assembly are generally similar to those of the previously described embodiments, with the exception of several differences which will be described below.

As illustrated in FIG. 9A, a pair of piston-type motors 6A and 6B of the type generally indicated in FIGS. 1A through 1C and 5, are fixedly installed within respective motor cavities 30A and 30B of housing 2. Each piston-type motor 6A and 6B has a respective chamber housing and movable piston, indicated by 31A and 31B, and 34A and 34B, respectively. Actuation elements 37A and 37B are fixedly connected to respective pistons 34A and 34B and project through respective elongated slots 38A and 38B formed in cannula cavity wall 22; this is achieved, in a manner similar to that described in connection with the embodiments shown in FIGS. 1A through 1C, 4A, 4B and 5. While not shown in FIG. 9A, preferably a rod or bar is fixedly attached between actuation elements 37A and 37B in order to maintain them a fixed distance apart, and yet provide an operable connection between the inner cannula 4' and actuation elements 37A and 37B in the manner described below. As shown in FIG. 9B, this embodiment includes hinged cover panel 21 in a manner similar to that described in the embodiments of FIGS. 1A, 1C, 5, 6A and 8A.

As illustrated in FIG. 9A, inner cannula base 10'" has first and second receiving slots or notches 12A and 12B, into which extensions 13A and 13B of respective actuation elements 37A and 37B are received. Such operable connections between movable pistons 6A and 6B and inner cannula base 10'" enables inner cannula 4' to reciprocate relative to housing 2 when actuation elements 37A and 37B are caused to reciprocate relative to respective gas driven motors 6A and 6B.

In order to control the filling and venting of chambers 33A and 33B of the first and second piston motors, to effectuate cyclical reciprocating motion of actuation elements 37A and 37B and thus inner cannula 4', a mechanically-operated gas flow control device 90 is provided. As shown in FIG. 9A, gas flow control device 90 is employed in operable association with an external source of pressurized gas (not shown), gas inlet ports 32A and 32B, and movable pistons 34A and 34B.

As illustrated in greater detail in FIGS. 9C and 9D, gas flow control device 90 comprises a shuttle valve housing or casing 91, having first and second shuttle chambers 92A and 92B. These shuttle chambers are separated by a shuttle valve member 93 which is fixedly attached to a slidable shaft 94. As illustrated, shuttle valve member 93 is slidable between two positions or states "A" and "B". In order to achieve this shaft 94 extends through bores 95A and 95B formed in shuttle chamber end walls 91A and 91B respectively, in which seals 96A and 96B are installed in a conventional manner. When the shuttle valve 93 is centrally disposed in casing 91 between states A and B, shaft ends 94A and 94B protrude equally beyond respective bores 95A and 95B.

Adjacent one end of cylindrical shuttle chamber side wall 98, a first gas exit port 89A is formed, whereas adjacent the other end of wall 98, a second gas exit port 98B is formed, as shown. At about intermediate the end walls, a gas inlet port 100 is formed in shuttle chamber side wall 98. A pair of annulus-shaped shuttle valve stops 101A and 101B are formed at opposite end portions of the interior surface of cylindrical wall 98. These stops 101A and 101B serve to limit sliding movement of shuttle valve 93 when shaft 94 is displaced in one of two possible axial directions by actuation elements 37A and 37B, respectively, as shown in FIG. 9A. As will be discussed in greater detail hereinafter, it is these actuation elements 37A and 37B which displace shaft 94 and thus shuttle valve 93 between one of two states, as movable pistons 34A and 34B are caused to reciprocate.

Preferably, at least a portion of shuttle valve 93 is formed of a ferromagnetic material so that ferrous end walls 102A and 102B will attract ferromagnetic shuttle valve 93 and pull it against one of stops 101A and 101B and into gas flow state A or B, i.e., when shuttle valve 93 is brought into proximity therewith upon displacement of shaft 94 by one of actuation elements 37A and 37B. Peripheral side surfaces of shuttle valve 93 are provided with seals 103 to prevent gas leakage between shuttle chambers 92A and 92B.

As illustrated in FIG. 9A, first gas exit port 99A of device 90 is in a fluid communication with second chamber housing 31B by gas channel 104, whereas second gas exit port 99B is in fluid communication with first chamber housing 31A by gas channel 105. In the illustrated embodiment, gas inlet aperture 106 is formed through housing 2 and permits gas channel 107 to establish fluid communication between gas inlet port 100 and the external source of pressurized gas. Notably, chamber housings 31A and 31B, shuttle valve housing 91, gas channels 104, 105 and 107 can be realized as discrete elements, as shown, or alternatively as integrally formed elements which are part of the interior of the hand-holdable housing itself.

The principal function of gas flow control device 90 is to control the flow of gas to pistons 34A and 34B so that only one of the gas pistons is actively driven at a time, while the other is passively driven. The manner of operation of gas flow control device 90 in cooperation with the periodic displacement of pistons 34A and 34B, will now be described.

Owning to the fact that shuttle valve 93 is magnetically biased to be in essentially one of two possible positions, or gas flow states, gas will initially be caused to flow into one of piston-chamber housings 31A or 31B, and cause its respective piston and actuation element to move away (i.e., protract) from its respective chamber housing. Only along a small portion of the piston excursion will shuttle valve shaft 94 and thus shuttle valve 93, be displaced within shuttle valve housing 91 as the actively driven piston is displaced upon buildup of pressurized gas within its respective chamber.

To illustrate this cyclical process, it will be assumed that gas flow control valve 90 is initially in state A, as shown in FIG. 9A. Here, piston 34A has reached its maximal displacement and pressurized gas within chamber 33A has been substantially vented through gas outlet port 26A and through ports 39A and 39B. In this position (state A), shuttle valve 90 is magnetically biased against stops 101B so that gas is caused to flow from the external gas source (not shown), through first shuttle chamber 92A and into second chamber housing 33B. With shuttle valve 93 in this state, gas pressure is allowed to build up in chamber 33B, displacing piston 34B and actuation element 37B to protract from second chamber housing 31B. Therewhile, inner cannula base 10''' is caused to undergo an outwardly directed excursion within cannula cavity 20, commensurate with the active displacement of piston 34B. During piston excursion (i.e., travel) defined over length $L_1$, shuttle valve 93 remains in state A against stop 101B.

Then over piston excursion $L_2$, actuation element 37B contacts shaft end 94B and displaces shuttle valve 93 away from stop 101B to about mid-position in shuttle housing 91, approximately over input port 100, at which point, magnetic shuttle valve 93 is pulled toward ferrous plate 102A into state B and against stop 101A, as shown in FIG. 9A with phantom lines. At this phase in the cycle, piston 34A is fully retracted within chamber housing 31A, while piston 34B is fully protracted from chamber housing 31B and displaced a distance $L_3$ from the upper portion thereof (i.e., $L_3=L_1+L_2$). In State B, gas flow control device 90 directs the flow of pressurized gas from the external source, along channel 107, through second shuttle chamber 92B and along channel 105 and into piston chamber housing 31A.

Magnetically biased shuttle valve 93 remains in state B as chamber housing 31A fills with pressurized gas, expanding the chamber 33A and actively displacing piston 34A away from chamber housing 31A, while causing piston 34B to passively retract back into its chamber housing 31B. All the while, inner cannula base 10''', being operably associated with actuation elements 37A and 37B, undergoes a commensurate amount of inwardly directed excursion within cannula cavity 20. When piston 34B is displaced an amount of distance $L_4$, actuation element 37A contacts shaft end 94A and displaces shuttle valve 93 a small distance $L_5$, at which point, magnetic shuttle valve 93 is pulled towards ferrous plate 102B, back into state A and against stop 101B. At this phase in the cycle, piston 34B is fully retracted within chamber housing 31B while piston 34A is fully protracted from chamber housing 31A and displaced at a distance $L_6$ from the upper portion thereof (i.e., $L_6=L_4+L_5$). In state A, gas flow control device 90 directs the flow of pressurized gas from the external source, along channel 107, through first shuttle chamber 92A, along channel 104 and into piston chamber housing 31B.

Magnetically biased shuttle valve 93 remains in state A as chamber housing 91B fills with pressurized gas, expanding chamber 3B actively displacing piston 34B away from chamber housing 31B, while causing piston 34A to passively retract back into its piston chamber housing 31A. All the while, inner cannula base 10''', being operably associated with actuation elements 37A and 37B, undergoes once again a commensurate amount of outwardly directed excursion within cannula cavity 20. With a preselected gas pressure and flow rate set at gas inlet port 100 of device 90, the above-described process of gas filling, venting and flow control occurs automatically at a corresponding rate, resulting in periodic reciprocation of inner cannula 10''' relative to hand-holdable housing 2. In turn, this periodic reciprocation of inner cannula 4' results in periodic displacement of the general location of aspiration occurring along the length of the cannula assembly.

Referring to FIGS. 12A through 12F, there is illustrated yet a seventh embodiment of the liposuction device of the present invention. In general, liposuction device 1G has a pistol-shaped housing 110 which comprises a barrel portion 111 and a detachable handle portion 112. Instead of using a reciprocating piston motor to translate inner cannula 4' relative to housing 100, this embodiment utilizes a rotary-type motor 113. In operative association with a cam mechanism, generally indicated by reference numeral 114, rotary-type motor 113 causes actuation element 115 to cyclically slide back and forth and cause inner cannula 4' to periodically reciprocate relative to barrel portion 111 of the pistol-shaped housing.

As illustrated in FIGS. 12B through 12D, barrel portion 111 of the housing comprises a cannula cavity 116 adapted for slidably receiving cylindrically-shaped base 17 of inner cannula 4', in a manner described hereinabove. Cannula cavity 116 is also provided with a longitudinally extending access opening, over which a hingedly connected cover panel 117 is provided. As illustrated in FIG. 12E, cover panel 117 facilitates insertion of the cannula assembly into, and removal of the cannula assembly from, cannula cavity 116 in a manner similar to that described in connection with liposuction instrument 1A of FIGS. 1A through 1C, in particular. As illustrated in FIG. 12C in greater detail, inner cannula base 10 is adapted to be received within cannula cavity 116 and outer cannula base flange 19 releasably received within annular recess 118 formed in cannula cavity wall 22.

To install inner cannula 4' into cannula cavity 116, semiflexible transparent tubing 15 is connected to inner cannula outlet port 11. Then cover panel 117 is opened and tubing 15 fed out through rear port 119 of the barrel portion, as illustrated in FIGS. 12C and 12F. Inner cannula base 10 is then slid into cavity 116 with extensional portion of actuation element 115 received in notch 12. Then outer cannula 5' is slid over the distal end of inner cannula 4' until outer cannula base 17 is received within annular recess 118. Thereafter, as shown in FIG. 12E, cover panel 117 is snapped closed using, for example, a spring biased locking device 120, of the type previously described above. Removal of inner and outer cannulas simply involves a reversal of the above procedure.

Alternatively, using spring biased actuation elements and inner and outer cannulas of the type shown in FIGS. 4A and 4B, barrel portion 111 can be realized without necessity of hinged cover panel 117. In such an alternative embodiment, the inner and outer cannulas can be snap-fitted into and pulled out of cannula cavity 116 in a manner similar to that described hereinabove.

As illustrated in FIGS. 12B through 12F, barrel portion 111 houses cam mechanism 114 which is operably associated with (i) rotary motor 113 contained within the handle portion, and (ii) actuation element 115 which slidably passes through a longitudinal slot 121 formed within the upper wall of cannula cavity 116. As in the other previously described embodiments, actuation element 115 includes extension 115A that passes through elongated slot 121 and is received within notch 12 formed in inner cannula base 10. In addition, cam mechanism 114 of the illustrated embodiment inherently embodies gear reduction. In this way, a high angular shaft velocity of rotary motor 113, can be efficiently transformed into reciprocational strokes of the cannula, occurring at a substantially lower rate. With such an arrangement, as rotary motor 113 is caused to rotate under either gas pressure or electrical power, actuation element 115 is caused to reciprocate within elongated slot 121 by way of cam mechanism 114, and thereby cause inner cannula 4' to periodically reciprocate relative to housing 110. This motion results in periodic displacement of the general location of aspiration occurring along the length of the cannula assembly.

As illustrated in FIGS. 12B and 12C, cam mechanism 114 of the preferred embodiment comprises a drive wheel 122 having a first predetermined number of gear teeth 123 disposed thereabout. Drive wheel 122 is rotatably mounted to a shaft 124 mounted through and opening in the top panel of an accommodating section 125 of the barrel portion. Cam mechanism 114 also includes a connective element 126 having first and second ends 126A and 126B, respectively. First end 126A of the connective element is pivotally attached to the drive wheel 122 at a point disposed away from the axial center 124, whereas second end 126B is pivotally connected to actuation element 115 as shown. In order to adjust the distance away from the axis of rotation 124 at which the first end of the connective element is pivotally attached, a radially formed slot 127 is formed in drive wheel 122. A plurality of widened circular apertures 128 are disposed along radial slot 127 as shown in FIGS. 12B and 12D. In this way, a spring-loaded cylindrical pin 129 passing through the first end of connective element 126, can be selectively locked into one of apertures 128 by pulling upwardly upon pin 129 and setting its cylindrical base 129A into the desired aperture 128.

In FIG. 12D, pin 129 is shown to further include pin head 129B, a hollow bore 129B, and an axle 129D having heads 129E and 129F. As shown, a spring 129G is enclosed within bore 129C, about axle 129D and between head 129F and an inner flange 129H. By selectively locking the first end 126A of connective element 126 into a particular circular notch 128 using spring loaded pin 129, the distance of the first end of the connective element from axial center 124 can be set, and thus the amount of inner cannula excursion (and effective aspiration aperture displacement) thereby selected. To permit access to spring-loaded pin 129, the top panel of accommodating portion 125 of the housing is provided with a hinged door 132 that can be opened and snapped closed as desired.

As illustrated in FIGS. 12B and 12C, handle portion 112 of the housing encloses a substantial portion of rotary motor 113 whose shaft 133 projects beyond the handle portion and bears a gear wheel 134. As shown, gear wheel 134 has a second predetermined number of gear teeth 134A disposed circumferentially thereabout, which mesh with drive wheel teeth 123. Notably, to permit the rear portion 119 of cannula cavity 116 to extend all the way towards the rear of the barrel portion for passage and exit of aspiration hose 15, shaft 133 of the motor is mounted off center of handle portion 113, as shown in FIGS. 12C and 12F.

Rotary motor 113 is preferably an electric motor whose shaft speed is controllable by the voltage applied to its terminals. Such speed control can be realized by a conventional speed control circuit 135 connected between motor 113 and a conventional 110–115 volt, 50–60 Hertz power supply. As illustrated in FIG. 12C, conventional electrical cord 136 and on/off power switch 150 can be used to connect control circuit 135 and the power supply. Control over the output voltage produced from speed control circuit 115 and provided to electrical motor 113, can be adjusted, for example, by changing the resistance of a potentiometer 137 which is operably connected to the speed control circuit. As shown in FIG. 9C in particular, this potentiometer 137 can be embodied within a trigger mechanism 138 which is connected, for example, to handle portion 112 of housing 110. By pulling trigger 138, the speed of rotary motor 113 can be controlled, and consequently, so too the rate of reciprocation of inner cannula 4' relative to outer cannula 5', and thus the rate of displacement of the effective aspiration apertures.

To connect handle portion 112 to barrel portion 111 and permit disconnection therebetween for cleaning, sterilization and general service, handle portion 112 is provided with flange 140 and thumb-operable spring element 141. Barrel portion 111, on the other hand, is provided with slot 142, catch 143, and cavity 144. To connect handle portion 112 to barrel portion 111, shaft 133 is vertically passed through channels 144 and 145 until gear 134 is slightly below the plane of drive wheel 122. Then, spring element 141 is inserted within cavity 144 while flange 140 is guided into slot 142. By pushing the rear portion of handle 112 in the longitudinal direction of cannula cavity 116, spring element 141 will snap over and clasp catch 143 as shown in FIG. 12C. In this configuration, handle portion 112 is secured to barrel portion 111 and gear teeth 123 will mesh with drive wheel teeth 134A. To disconnect handle portion 112 from barrel portion 11, the surgeon's thumb simply depresses spring-element 141 downwardly and then, by moving handle portion 112 slightly rearwardly, then downwardly, flange 140 is dislodged from slot 142 and motor shaft 133 can be withdrawn from channels 144 and 145. In this disassembled state, handle portion 110 and barrel portion 112 can be individually cleaned and sterilized using conventional procedures known in the surgical instrument art.

Liposuction device 1G described above employed an electric rotary motor to effectuate reciprocation of inner cannula 4' relative to housing 110. However, in an alternative embodiment, it is possible to effect reciprocation of the outer cannula while the inner cannula is stationary with respect to the housing, as shown in FIGS. 6A through 7. Also, it is possible to employ a conventional gas driven rotary motor in lieu of electric rotary motor 113. In such an embodiment, trigger 138 can be operatively associated with a gas flow control valve. Thus, by controlling the rate of gas flow to the gas rotary motor upon actuation of trigger 138, the angular velocity of shaft 133 can be controlled and thus the rate of reciprocation of inner cannula 4' relative to housing 110.

Having described various illustrated embodiments, it is appropriate at this juncture to describe the method of the present invention using, for purposes of illustration only, the liposuction instrument 1C illustrated in FIG. 5.

In general, the surgeon prepares in a conventional manner, the area of skin below which liposuction is to be performed. Typically, this entails marking various zones where radial displacement of the aspiration apertures are to occur. Liposuction instrument 1C of the present invention is assembled as described above so that aspiration apertures 8A', 8B' and 8C' of cannula assembly 3' are in communication with a vacuum source (not shown). A small incision is then made in the patient's skin in al conventional manner, and the distal portion of the cannula assembly is inserted into a premarked radial zone. As pressurized gas is provided to piston motor 6, inner cannula 10 will automatically reciprocate causing the general location of the suction apertures to be automatically displaced along each tunnel of fatty tissue. During the operation of the instrument, the surgeon's hand holding the liposuction instrument is maintained essentially stationary with respect to the patient. Fatty tissue is aspirated through the periodically displaced aspiration apertures, and transferred into a reservoir tank operably associated with the vacuum source.

As deemed necessary, the surgeon can selectively increase the rate of aspiration aperture travel along the distal end of the cannula assembly. This can be achieved by a foot-operated gas flow control device 78 which controls the rate of gas flow to piston motor 6. Also, the amount of inner cannula excursion (i.e., aspiration aperture travel) can also be selected by adjusting the compliance of spring 40 through rotation of threaded element 42.

While the particular embodiments shown and described above have proven to be useful in many applications in the liposuction art, further modifications of the present invention herein disclosed will occur to persons skilled in the art to which the present invention pertains. All such modifications are deemed to be within the scope and spirit of the present invention defined by the appended claims.

What is claimed is:

1. A powered liposuction device comprising:
   (a) A hand-holdable housing having a longitudinal extent, a cylindrically-shaped cannula cavity extending along a substantial portion of said longitudinal extent, and a reciprocation means reciprocatable within said hand-holdable housing and an actuation means; and;
   (b) a cannula assembly operably connectable to said hand-holdable housing, and including;
      (1) a hollow inner cannula having a distal end, and a proximal end, and at least one inner suction aperture about said inner cannula distal end, said inner cannula proximal end further including an outlet port and a continuous passageway communicating said inner suction aperture with said outlet port, said inner cannula having an inner cannula base portion extending from said inner cannula proximal end and being releasably connectable to said hand-holdable housing, when said inner cannula base portion is slidably disposed within said cannula cavity.
      (2) a hollow outer cannula having a distal end, a proximal end, and at least one outer elongated suction aperture disposed about said outer cannula distal end, said outer cannula having an outer cannula base extending from said outer cannula proximal end, and said hollow inner cannula being disposed within at least a portion of said hollow outer cannula so as to enable relative sliding movement between said hollow outer and inner cannulas while permitting aspiration through said outer and inner suction apertures, along said continuous passageway and out of said outlet port, said inner suction aperture being elongated in the longitudinal direction of said hollow inner cannula, said inner suction aperture being substantially shorter than said outer suction aperture alone said longitudinal direction,
      (3) alignment means, operably associated with said hollow inner cannula, for aligning said hollow inner and out cannulas so that said inner suction aperture is in registration with at least a portion of said outer elongated suction aperture as said hollow inner and outer cannulas are caused to undergo said relative sliding movement, and
      (4) said hollow inner cannula being operably associated with said actuation means, and said hollow outer cannula being supportable in an essentially stationary position with respect to said hand-holdable housing so that said actuation means can effectuate relative sliding movement between said hollow inner and outer cannulas when said reciprocation means reciprocates, and that the location of said aspiration is periodically displaceable a distance equal to a substantial portion of the longitudinal extent of said hand-holding housing.

2. A powered liposuction device comprising:
   (A) a hand-holdable housing having a longitudinal extent, a cannula cavity extending along a substantial portion of said longitudinal extent, and a reciprocation means reciprocatable within said hand-holdable housing and being provided with an actuation means, and
   (B) a cannula assembly operably connectable to said hand-holdable housing, and including:
      (1) a hollow inner cannula having a distal end, a proximal end, and at least one inner suction aperture about said inner cannula distal end, said inner cannula proximal end further including an outlet port and a continuous passageway communicating said inner suction aperture with said outlet port, said inner cannula having an inner cannula base portion extending from said inner cannula proximal end and having a connection means for releasably snap-fitting said inner cannula base portion with said actuation means when said inner cannula base portion is slidably disposed within said cannula cavity,
      (2) a hollow outer cannula having a distal end, a proximal end, at least one elongated outer suction aperture about said outer cannula distal end, said outer cannula having an outer cannula base extending from said outer cannula proximal end, said hollow inner cannula being disposed within at least a portion of said hollow outer cannula so as to enable relative sliding movement between said hollow outer and inner cannulas while permitting aspiration through said outer and inner suction apertures, along said continuous passageway and out of said outlet port, and said inner suction aperture being elongated in the longitudinal direction of said hollow inner cannula and said inner suction aperture being substantially shorter than said outer suction aperture along said longitudinal direction,
      (3) alignment means operatively associated with one of said inner and outer cannula for aligning said hollow inner and outer cannulas so that said inner suction aperture is in registration with at least a portion of said outer elongated suction aperture as said hollow inner and outer cannulas are caused to undergo said relative sliding movement, and
      (4) said hollow inner cannula being operably associated with said actuation means, and said hollow outer cannula being supportable in an essentially stationary position with respect to said hand-holdable housing so that said actuation means can effectuate relative sliding movement between said hollow inner and outer cannulas when said reciprocation means reciprocates, and that the location of said aspiration is periodically displaceable a distance equal to a substantial portion of the longitudinal extent of said hand-holdable housing.

3. Apparatus for use in suction assisted tissue curettage, comprising:

a hand-holdable housing having a longitudinal extent, first and second openings disposed along said longitudinal extent, a first cavity including an interiorly disposed sidewall surface and extending along a substantial portion of said longitudinal extent and between said first and second opening, and a second cavity disposed alongside at least a portion of said first cavity;

a cannula assembly including a hollow inner cannula having a least one inner suction aperture, and a hollow outer cannula having at least one outer suction aperture, said hollow outer cannula being stationarily mounted with respect to said first opening, and said hollow inner cannula being positionable within at least a portion of said hollow outer cannula so as to enable sliding movement between said hollow outer and inner cannulas while permitting aspiration through said outer and inner suction apertures, and said hollow inner cannula having an outlet port for connecting a section of tubing which extends along said first cavity and out said second opening;

alignment means operatively associated with one of said inner and outer cannulas for aligning said hollow inner and outer cannulas so that said inner suction aperture is in registration with at least a portion of said outer suction aperture as said hollow inner and outer cannulas are caused to undergo said sliding movement;

reciprocation means disposed within said second cavity; and an actuation means operably associated with said reciprocation means and extending through said interiorly disposed sidewall surface and into a portion of said first cavity and being adapted to engage with a portion of said hollow inner cannula so as to operably associate said reciprocation means with said hollow inner cannula and effectuate relative sliding movement between said hollow inner and outer cannulas when said reciprocation means cause said actuation means to reciprocate and cause the location of said aspiration through said outer and inner suction apertures to be periodically displaced a distance predetermined by the user of said apparatus.

4. The apparatus of claim 3, wherein said distance is equal to a substantial portion of the longitudinal extent of said hand-holdable housing.

* * * * *